US010006053B2

(12) United States Patent
Baltimore et al.

(10) Patent No.: US 10,006,053 B2
(45) Date of Patent: Jun. 26, 2018

(54) USE OF CHIMERIC NUCLEASES TO STIMULATE GENE TARGETING

(71) Applicant: California Institute of Technology, Pasadena, CA (US)

(72) Inventors: David Baltimore, Pasadena, CA (US); Matthew Porteus, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days. days.

(21) Appl. No.: 15/259,848

(22) Filed: Sep. 8, 2016

(65) Prior Publication Data

US 2017/0114368 A1   Apr. 27, 2017

Related U.S. Application Data

(63) Continuation of application No. 10/656,531, filed on Sep. 5, 2003, now Pat. No. 9,447,434.

(60) Provisional application No. 60/408,454, filed on Sep. 5, 2002, provisional application No. 60/419,341, filed on Oct. 17, 2002, provisional application No. 60/484,788, filed on Jul. 3, 2003.

(51) Int. Cl.
    *C12N 15/90*   (2006.01)
(52) U.S. Cl.
    CPC ........ *C12N 15/907* (2013.01); *C12N 2800/80* (2013.01); *C12N 2830/002* (2013.01)
(58) Field of Classification Search
    CPC ............ C12N 15/907; C12N 2830/002; C12N 2800/80
    See application file for complete search history.

(56) References Cited

U.S. PATENT DOCUMENTS

| 4,665,184 A | 5/1987 | Dervan et al. |
| 4,795,700 A | 1/1989 | Dervan et al. |
| 4,942,227 A | 7/1990 | Dervan et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,789,155 A | 8/1998 | Dervan et al. |
| 5,789,538 A | 8/1998 | Rebar et al. |
| 5,792,640 A | 8/1998 | Chandrasegaran |
| 5,916,794 A | 6/1999 | Chandrasegaran |
| 5,945,577 A | 8/1999 | Stice et al. |
| 5,955,341 A | 9/1999 | Kang et al. |
| 6,007,988 A | 12/1999 | Choo et al. |
| 6,013,453 A | 1/2000 | Choo et al. |
| 6,077,710 A | 6/2000 | Susko-Parrish et al. |
| 6,140,081 A | 10/2000 | Barbas et al. |
| 6,140,466 A | 10/2000 | Barbas et al. |
| 6,147,276 A | 10/2000 | Campbell et al. |
| 6,242,568 B1 | 6/2001 | Barbas et al. |
| 6,265,196 B1 | 7/2001 | Chandrasegaran |
| 6,326,166 B1 | 12/2001 | Pomerantz et al. |
| 6,331,658 B1 | 12/2001 | Cooper et al. |
| 6,453,242 B1 | 9/2002 | Eisenberg et al. |
| 6,479,626 B1 | 11/2002 | Kim et al. |
| 6,534,261 B1 | 3/2003 | Cox et al. |
| 2002/0022021 A1 | 2/2002 | Emerson |
| 2002/0107214 A1 | 8/2002 | Choulika et al. |
| 2002/0110898 A1 | 8/2002 | Choulika et al. |
| 2002/0152488 A1 | 10/2002 | Cooper et al. |
| 2003/0131365 A1 | 7/2003 | Cooper et al. |
| 2003/0232410 A1 | 12/2003 | Liljedahl et al. |
| 2004/0019002 A1 | 1/2004 | Choulika et al. |
| 2004/0121357 A1 | 6/2004 | Franklin |

FOREIGN PATENT DOCUMENTS

| EP | 0957165 B1 | 11/1999 |
| WO | WO 95/09233 A1 | 4/1995 |
| WO | WO 96/40882 A1 | 12/1996 |
| WO | WO 97/47758 A1 | 12/1997 |
| WO | WO 98/53058 A1 | 11/1998 |
| WO | WO 98/53059 A1 | 11/1998 |
| WO | WO 98/53060 A1 | 11/1998 |
| WO | WO 00/09755 A2 | 2/2000 |
| WO | WO 00/28008 A1 | 5/2000 |
| WO | WO 00/42219 A1 | 7/2000 |
| WO | WO 00/46385 A1 | 8/2000 |
| WO | WO 00/46386 A2 | 8/2000 |
| WO | WO 00/63365 A1 | 10/2000 |
| WO | WO 01/05961 A1 | 1/2001 |
| WO | WO 01/19981 A2 | 3/2001 |
| WO | WO 01/40798 A2 | 6/2001 |
| WO | WO 01/66717 A2 | 9/2001 |
| WO | WO 02/04488 A2 | 1/2002 |
| WO | WO 03/80809 A2 | 10/2003 |
| WO | WO 03/87341 A2 | 10/2003 |

OTHER PUBLICATIONS

Urnov et al., Nature 435:646-651, 2005.*
Gardlik et al., Med. Sci. Monit. 11(4):RA110-121, 2005.*
Phillips, A., J. Pharm. Pharmacology 53:1169-1174, 2001.*
Porteus et al., Nature Biotechnology 23(8):967-973, 2005.*
Takeuchi et al., Biochemical and Biophysical Research Communications 293:953-957, 2002.*
McCune et al., PNAS 91:9852-9856, 1994.*
Smih et al., Nucleic Acids Research 23(24):5012-5019, 1995.*
Abremski, et al., "Bacteriophage PI Site-Specific Recombination," *J. of Biological Chemistry* 259:1509-1514 (1984).

(Continued)

*Primary Examiner* — Delia Ramirez
(74) *Attorney, Agent, or Firm* — Pasternak Patent Law

(57) ABSTRACT

Gene targeting is a technique to introduce genetic change into one or more specific locations in the genome of a cell. For example, gene targeting can introduce genetic change by modifying, repairing, attenuating or inactivating a target gene or other chromosomal DNA. In one aspect, this disclosure relates to methods and compositions for gene targeting with high efficiency in a cell. This disclosure also relates to methods of treating or preventing a genetic disease in an individual in need thereof. Further disclosed are chimeric nucleases and vectors encoding chimeric nucleases.

16 Claims, 18 Drawing Sheets

(56) References Cited

OTHER PUBLICATIONS

Aggarwal and Wah, "Novel Site-Specific DNA Endonucleases," *Curr. Opinion in Struct. Biol.* 8:19-25 (1998).
Akopian, et al., "Chimeric Recombinases With Designed DNA Sequence Recognition," *Proc. Natl. Acad. Sci. USA* 100:8688-8691 (2003).
Baubonis, et al., "Genomic Targeting With Purified CRE Recombinase," *Nucleic Acids Res.* 21:2025-2029 (1993).
Beerli et al., "Engineering Polydactyl Zinc-Finger Transcription Factors," *Nature Biotechnology* 20:135-141 (2002).
Bibikova, et al. "Stimulation of Homologous Recombination Through Targeted Cleavage by Chimeric Nucleases," *Molecular and Cellular Biology* 21(1):289-297 (2001).
Bibikova, et al. "Targeted Chromosomal Cleavage and Mutagenesis in *Drosphila* using Zinc-Finger Nucleases," *Genetics* 161:1169-75 (2002).
Bibikova, et al., "Enhancing Gene Targeting With Designed Zinc Finger Nucleases," *Science* 300:764 (2003).
Bitinate, et al., "Fold Dimerization is Required for DNA Cleavage," *Proc. Natl. Acad. Sci. USA* 95:10570-10575 (1998).
Brenneman, M. et al. "Stimulation of Intrachromosomal Homologous Recombination in Human Cells by Electroporation With Site-Specific Endonucleases," *Proc. Natl Acad. Sci. USA* 93:3608-12 (1996).
Brisson, et al., "Expression of a Bacterial Gene in Plants by Using a Viral Vector," *Nature* 310:511-514 (1984).
Broglie, et al., "Right-Regulated Expression of a PEA Ribulose-1,5-Bisphosphate Carboxylase Small Subunit Gene in Transformed Plant Cells," *Science* 224:838-843 (1984).
Campbell, et al., "Sheep Cloned by Nuclear Transfer From a Cultured Cell Line," *Nature* 380:64-66 (1996).
Capecchi, "Altering the Genome by Homologous Recombination," *Science* 224:1288-1292 (1989).
Chandrasegaran S. et al., "Chimeric Restriction Enzymes: What is Next?," *J. Biol. Chem.* 380:841-8 (1999).
Chevalier, B. et al., "Design, Activity, and Structure of a Highly Specific Artificial Endonuclease," *Molecular Cell.* 10:895-905 (2002).
Choulika et al., "Induction of Homologous Recombination in Mammalian Chromosome by Using the I-SCEI System of *Saccharomyces Cerevisiae,*" *Molecular and Cellular Biology*, 15(4):1968-73 (1995).
Cohen-Tannoudji, et al., I-SCEI-Induced Gene Replacement at a Natural Locus in Embryonic Stem Cells, *Molecular and Cellular Biology*, 18(3):1444-48 (1998).
Coruzzi et al., "Tissue-Specific and Light-Regulated Expression of a PEA Nuclear Gene Encoding the Small Subunit of Ribulose-1,5-Bishophate Carboxylase," *The EMBO Journal* 3(8):1671-1679 (1984).
Desjarlais J.R. et al. "Toward Ruled Relating Zinc Finger Protein Sequences and DNA Binding Site Preferences," *Proc Natl. Acad. Sci. USA* 89:7345-49 (1992).
Desjarlais and Berg, "Use of a Zinc-Finger Consensus Sequence Framework and Specificity Rules to Design Specific DNA Binding Proteins," *Proc. Natl. Acad. Sci. USA* 90:2256-2260 (1993).
Donoho, et al. "Analysis of Gene Targeting and Intrachromosomal Homologous Recombination Stimulated by Genomic Double-Strand Breaks in Mouse Embryonic Stem Cells," *Molecular and Cellular Biology* 18(7):4070-4078 (1998).
Dreier, et al., "Development of Zinc Finger Domains for Recognition of the 5'-ANN-3'Family of DNA Sequences and Their Use in the Construction of Artificial Transcription Factors," *Journal of Biological Chemistry*, 276:31, 29466-078 (2001).
Elliott, et al., "Gene Conversion Tracts From Double-Strand Break Repair in Mammalian Cells," *Molecular and Cellular Biology*, 18(1):93-101 (1998).
Elrod-Erickson, et al., "Binding Studies With Mutants of Zif268," *The Journal of Biological Chemistry* 274(27):19281-19285 (1999).

Evans et al., "Establishment in Culture of Pluripotential Cells From Mouse Embryos," *Nature*, 292:154-156 (1981).
Ferguson-Smith, et al., "Imprinting and the Epigenetic Asymmetry Between Parental Genomes," *Science* 293:1086-1089 (2001).
Gorlich, et al., "Nucleocytoplasmic Transport," *Science* 271:1513-18 (1996).
Gowda et al., "Plant Gene Transfer," *J. Cell. Biochem*, 13D:301 (1989).
Greisman et al. "A General Strategy for Selecting High-Affinity Zinc Finger Proteins for Diverse DNA Target Sites," *Science* 275:657-61 (1997).
Gu, et al., "Independent Control of Immunoglobulin Switch Recombination at Individual Switch Regions Evidenced Through CRE-Ioxp-Mediated Gene Targeting," *Cell* 73:1155-1164 (1993).
Gu et al., "Deletion of a DNA Polymerase β Gene Segment in T Cells Using Cell Type-Specific Gene Targeting," *Science* 265:103-106 (1994).
Gurley, et al., "Upstream Sequences Required for Efficient Expression of a Soybean Heat Shock Gene," *Molecular and Cellular Biology* 6(2)559-565 (1986).
Hanson, et al., "Analysis of Biological Selections for High-Efficiency Gene Targeting," *Molecular and Cellular Biology* 15(1):45-51 (1995).
Hicks, et al., "Three Classes of Nuclear Import Signals Bind to Plant Nuclei," *Plant Physiol.* 107:1055-1058 (1995).
Huang, et al., "Splase: A New Class IIS Zinc-Finger Restriction Endonuclease With Specificity for SP1 Binding Sites," *Journal of Protein Chemistry* 15(5):481-489 (1996).
Jaenisch, "Transgenic Animals" *Science* 240:1468-1474 (1998).
Jakubauskas, et al., "Domain Organization and Functional Analysis of Type IIS Restriction Endonuclease Eco311," *Biochemistry* 47:8546-8556 (2008).
Jallepalli et al., "Securin is Required for Chromosomal Stability in Human Cells,"*Cell* 105:445-457 (2001).
Jasin, "Genetic Manipulation of Genomics With Rare-Cutting Endonucleases," *Trends Genet.* 12(6):224-228 (1996).
Jeggo et al., "Identification of Genes Involved in Repair of DNA Double-Strand Breaks in Mammalian Cells," *Radiation Research* 150:S80-S91 (1998).
Johnson, et al. "Double-Strand-Break-Induced Homologous Recombination in Mammalian Cells," *Biochemical Society Transactions* 29:196-201 (2001).
Khanna, et al. "DNA Double-Strand Breaks: Signaling, Repair and The Cancer Connection," *Nature Genetics.* 27:247-54 (2001).
Kim, et al., "Chimeric Restriction Endonuclease," *Proc. Natl. Acad. Sci. USA* 91:883-857 (1994).
Kim, et al., "Insertion and Deletion Mutants of FOK1 Restriction Endonuclease," *J. Biol., Chem.* 269:31978-31982 (1994).
Kim, et al., "Hydrid Restriction Enzymes: Zinc Finger Fusions to FOK I Cleavage Domain," *Proc., Natl. Acad, Sci. USA*, 93:1156-1160 (1996).
Kim et al., "Construction of a Z-DNA-Specific Restriction Endocnuclease," *Proc. Natl. Acad. Sci.* 94:12875-12879 (1997).
Kim, et al., "Chimeric Restriction Enzyme: GAL4 Fusion to FokI Cleavage Domain," *Journal Biological Chemistry* 379:489-495 (1998).
Klein, et al., "High-Velocity Microprojectiles for Delivering Nucleic Acids Into Living Cells," *Nature* 327:70-73 (1987).
Klein, et al., "Transformation of Microbes, Plants and Animals by Particle Bombardment," *Bio/Technology* 10:286-291 (1992).
Kuehn, et al., "A Potential Animal Model for Lesch-Nyhan Syndrome Through Introduction of HPRT Mutations Into Mice," *Nature* 326:295-298 (1987).
Lai, et al., "Production of α-1,3-Galctosyltransferase Knockout Pigs by Nuclear Transfer Cloning," *Science* 295:1089-1092 (2002).
Lee, et al., "Studying the Recruitment of SP1 to the β-Globin Promoter With an In Vivo Method: Protein Position Identification With Nuclease Tail (Pin Point)," *Proc. Natl. Acad. Sci. USA* 95:969-974 (1998).
Li et al., "Alteration of the Cleavage Distance of FOK I Restriction Endonuclease by Insertion Mutagenesis," *Proc. Natl. Acad. Sci. USA* 93:2764-2768 (1993).

(56) References Cited

OTHER PUBLICATIONS

Li, et al., "Functional Domains in FOK I Restriction Endonucleas," *Proc Natl. Acad. Sci. USA* 89:4275-4279 (1992).
Liu, Q. et al. "Validated Zinc Finger Protein Designs for All 16 GNN DNA Triplet Targets," *Journal if Biological Chemistry* 277(6)3850-56 (2002).
Mattaj, et al., "Nucleocytoplasmic Transport: The Soluble Phase," *Annu. Rev. Biochem.* 67:265-306 (1998).
McCreath, et al., "Production of Gene-Targeted Sheep by Nuclear Transfer From Cultured Somatic Cells," *Nature* 405:1066-1069 (2000).
Nahon, et al., "Targeting a Truncated Ho-Endonuclease of Yeast to Novel DNA Sites With Foreign Zinc Fingers," *Nucleic Acids Research* 26(5)1233-1239 (1998).
Odell, et al., "Identification of DNS Sequences Required for Activity of the Cauliflower Mosaic Virus 35S Promoter," *Nature* 313:810-812 (1985).
Pabo, et al., "Design and Selection of Novel $CYS_2HIS_2$ Zinc Finger Proteins," *Annu. Rev. Biochem.* 70:313-340 (2001).
Porteus, "Chimeric Nucleases Stimulate Gene Targeting in Human Cells," *Blood* from Nov. 16, 2002—as Abstract 821 from the 44th Annual Meeting of the American Society of Hematology in Philadelphia, PA (2002).
Porteus et al., "Efficient Gene Targeting Mediated by Adeno-Associated Virus and DNA Double-Strand Breaks," *Molecular and Cellular Biology* 23(10):3558-3565 (2003).
Porteus, et al., "Chimeric Nucleases Stimulate Gene Targeting in Human Cells," *Science* 300:763(2003).
Puchta et al., "Homologous Recombination in Plant Cells is Enhanced by In Vivo Induction of Double Strand Breaks Into DNA by a Site-Specific Endonucleases," *Nucleic Acids Research* 21(22):5034-5040 (1993).
Rebar, E. et al., "Zinc Finger Phage: Affinity Selection of Fingers With New DNA-Binding Specificities," *Science* 263:671-73 (1994).
Rideout III, et al., "Nuclear Cloning and Epigenetic Reprogramming of the Genome," *Science* 293:1093-1097 (2001).
Rouet, P. et al., "Expression of a Site-Specific Endonuclease Stimulates Homologous Recombination in Mammalian Cells," *Proc.Natl. Acad. Sci.* 91:6064-68 (1994).
Rouet, P. et al., "Introduction of Double-Strand Breaks Into the Genome of Mouse Cells by Expression of a Rare-Cutting Endonuclease," *Molecular and Cellular Biology* 14(12):8096-106 (1994).
Sanford, et al., "An Improved, Helium-Driven Biolistic Device," *Technique—A Journal of Methods in Cell and Molecular Biology* 3(1):3-16 (1991).
Sargent, et al., "Repair of Site-Specific Double-Strand Breaks in a Mammalian Chromosome by Homologous and Illegitimate Recombination," *Molecular and Cellular Biology* 17(1):267-277 (1997).
Schnieke, et al., "Human Factor IX Transgenic Sheep Produced by Transfer of Nuclei From Transfected Fetal Fibroblasts," *Science* 278:2130-2133 (1997).
Sedivy, et al., "Positwe Genetic Selection for Gene Disruption in Mammalian Cells by Homologous Recombination," *Proc. Natl. Acad. Sci. USA* 86:227-231 (1989).
Segal, et al., "Endonuclease-Induced, Targeted Homologous Extrachromosomal Recombination in *Xenopus* Oocytes," *Proc. Natl. Acad. Sci. USA* 92:806-810 (1995).

Segal, et al., "Toward Controlling Gene Expression at Will: Selection and Design of Zinc Finger Domains Recognizing Each of the 5'-GNN-3' DNA Target Sequences," *Proc. Natl. Acad. Sci. USA* 96:2758-2763 (1999).
Segal, D. J., "The Use of Zinc Finger Peptides to Study the Role of the Specific Factor Binding Sites in the Chromatin Environment," *Methods* 26:76-83 (2002).
Sera, et al., "Rational Design of Artificial Zinc-Finger Proteins Using a Nondegenerate Recognition Code Table," *Biochemistry* 41:7074-7081 (2002).
Sever, et al., "Heat-Inducible Hygromycin Resistance in Transgenic Tobacco," *Plant Molecular Biology* 15:827-833 (1990).
Shi, et al., "Specific DNA-RNA Hybrid Binding Zinc Finger Proteins," *Science* 268:282-284 (1995).
Shin, et al., "A Cat Cloned by Nuclear Transplantation," *Nature* 415:859 (2002).
Smih et al., "Double Strand Breaks at the target Locus Stimulate Gene Targeting in Embryonic Stem Cells," *Nucleic Acids Research* 23(24):5012-5019 (1995).
Smith, et al., "A Detailed Study of the Substrate of a Chimeric Restriction Enzyme," *Nucleic Acids Research* 27(2):674-681 (1999).
Smith, J. et al., "Requirements for Double-Strand Cleavage by Chimeric Restrictions Enzymes With Zinc Finger DNA-Recognition Domains," Nucleic Acids Research 28(17):3361-3369 (2000).
Stemberg, et al., "Bacteriophage P1 Site-Specific Recombination: I. Recombination Between Ioxp Sites," *Journal of Molecular Biology* 150:467-486 (1981).
Taghian, et al., "Chromosomal Double-Strand Breaks Induce Gene Conversion at High Frequency in Mammalian Cells," *Molecular and Cellular Biology* 17(11):6386-6393 (1997).
Takamatsu, et al., "Expression of Bacterial Chloramphenicol Acetyltransferase Gene in Tobacco Plants Mediated by TMV-RNA," *The EMBO Journal* 6:307-311 (1987).
Thierry, et al., "Cleavage of Yeast and Bacteriophage T7 Genomes at a Single Site Using the Rare Cutter Endonuclease I-sce I," *Nucleic Velten, Research* 19(1):189-190 (1991).
Velten, et al., "Isolation of a Dual Plant Promoter Fragment From the Ti Plasmid of *Agrobacterium tunefaciens*," *The EMBO Journal* 3(12):2723-2730 (1984).
Wah, et al., "Strucuture of The Multimodular Endonuclease FOK1 Bound to DNA," *Nature* 388:97-100 (1997).
Wilmut, et al.,"Viable Offspring Derived From Fetal and Adult Mammalian Cells," *Nature* 385:810-813 (1997).
Wilson, J. H., "Pointing Fingers at the Limiting Step in Gene Targeting," *Nature Biotechnology* 21(7):759-760 (2003).
Wolfe, et al., "Beyond the Recognition Code: Structures of Two $CYS_2$ $HIS_2$, Zinc Finger/TATA Box Complexes," *Structure* 9:717-723 (2001).
Wolfe, et al., "DNA Recognition by $CYS_2$ $HIS_2$ZINC Finger Proteins," *Annu., Rev. Biophys. Biomol. Struct.* 3:183-212 (1999).
Xu, et al., "Engineering a Endonuclease N. ALWL by Domain Swapping," *Proc. Natl. Acad. Sci, USA* 98(23):12990-12995 (2001).
Yanez, et al., "Therapeutic Gene Targeting," *Gene Therapy* 5:149-159 (1998).
Zufferey, et al., "Woodchuck Viruses Posttranscriptional Regulatory Element Enhances Expression of Transgenes Delivered by Retroviral Vectors," *Journal of Virology* 73(4):2886-2892 (1999).

\* cited by examiner

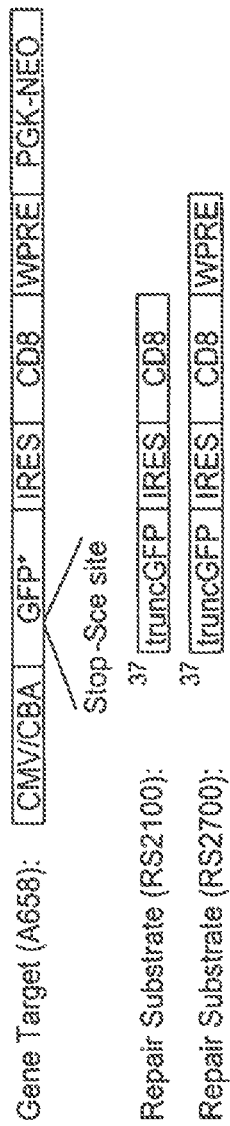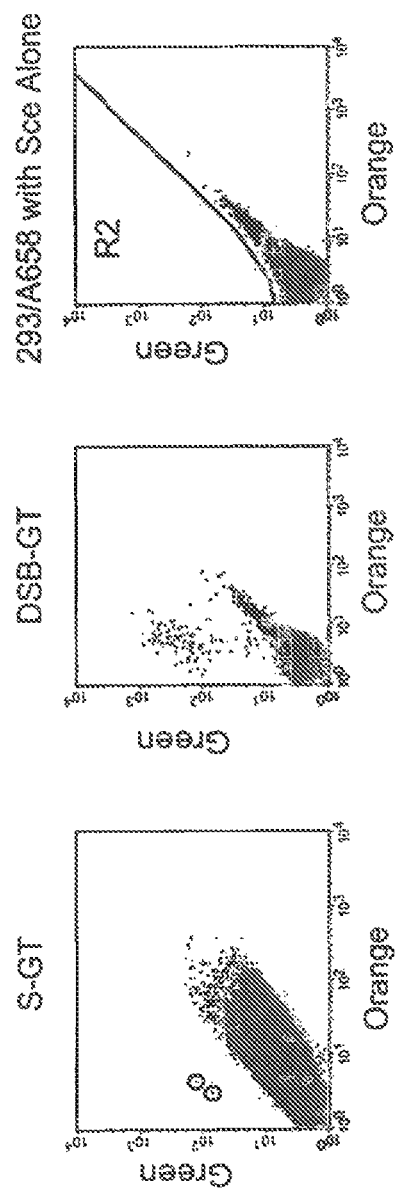
Fig. 1A
Fig. 1B

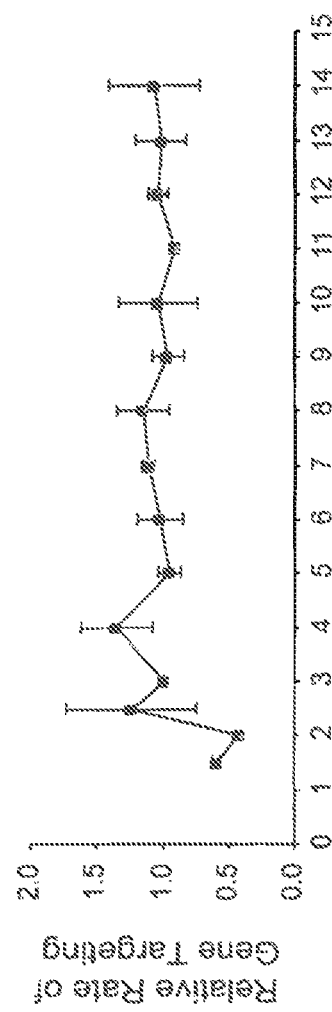

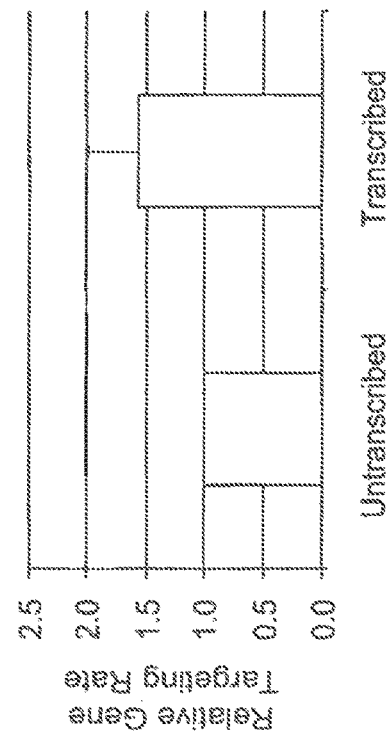
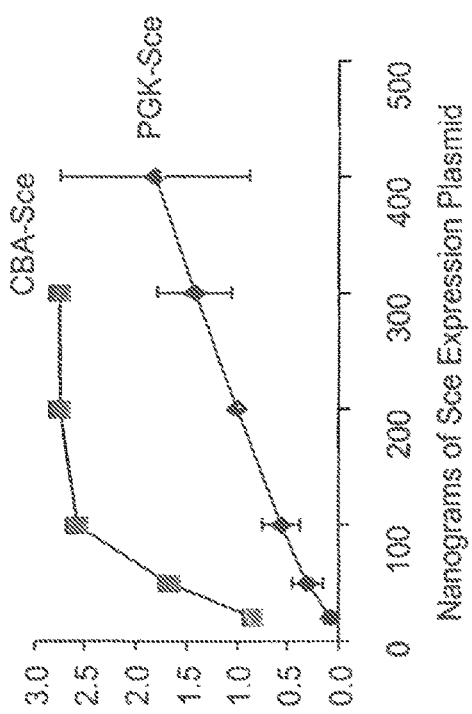
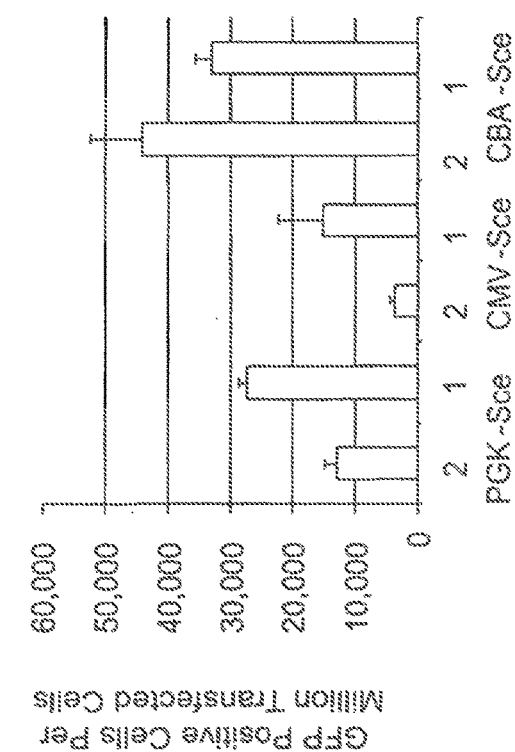

Targets:

QQR8: | 5' GFP | Stop | QQR Site 8 | HIS 800 | Sce Site | 3' GFP |

QQR6: | 5' GFP | Stop | QQR Site 6 | HIS 800 | Sce Site | 3' GFP |

QQRZif6: | 5' GFP | Stop | QQR Site 6 | Zif Site | Sce Site | 3' GFP |

Chimeric Nucleases:

CMV-QQR-L18-Fn: | CMV | ATG | N | QQR | L18 | Nuclease |

CMV-QQR-L0-Fn: | CMV | ATG | N | QQR | L0 | Nuclease |

CMV-Zif-L3-Fn: | CMV | ATG | N | Zif | L3 | Nuclease |

Fig. 3A

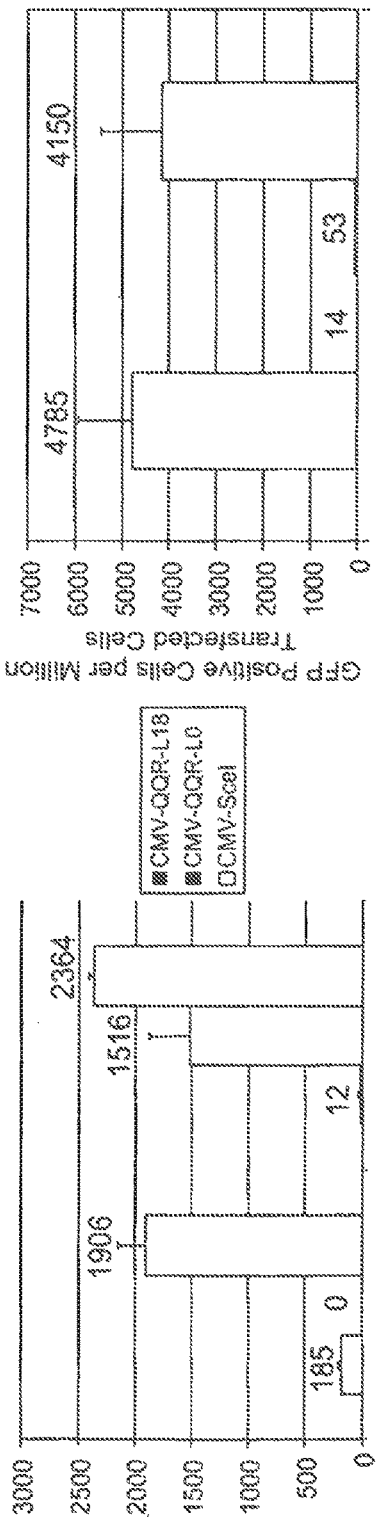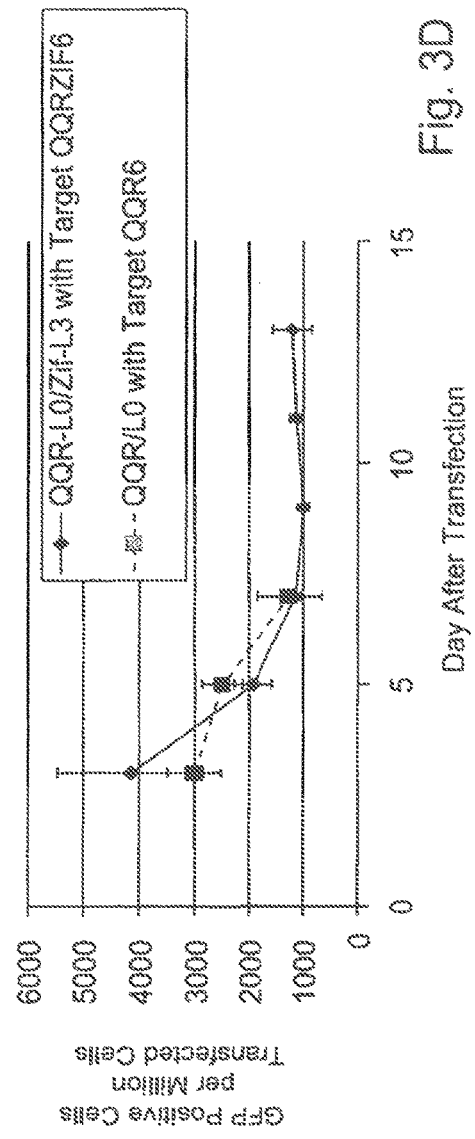

SEQ ID NO: 16
actAGCAACCTCaaacagACACCATGGtgcatctgactcctgaggagaagtctgccGTTACTGCCctgtgGGCAAGGTGaacg
tgatCGTTGGAGTtttgtcTGTGGTACCacgtagaactgaggactcctcttcagacggCAATGACGgacaccCCGTTCCACttgc HBGZF1  Fn    HBGZF2    Fn    HBGZF3    Fn    HBGZF4

Fig. 4

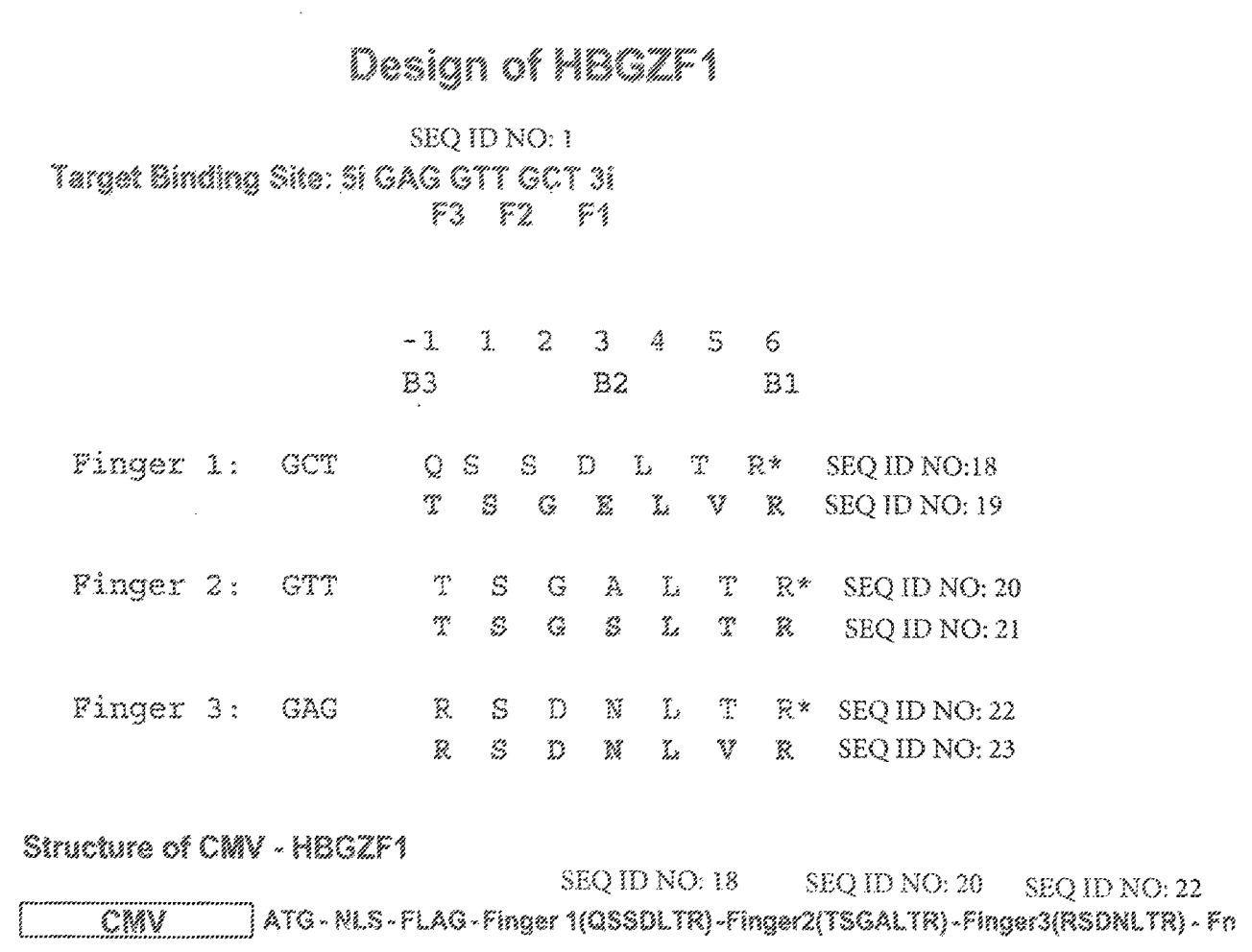

Design of HBGZF1

SEQ ID NO: 1
Target Binding Site: 5' GAG G

Design of HBGZF4

Target Binding Site: 5' GGC AAG GTG 3'  SEQ ID NO: 25
                         F3  F2  F1

|  |  | -1 | 1 | 2 | 3 | 4 | 5 | 6 |  |
|---|---|---|---|---|---|---|---|---|---|
|  |  | B3 |  |  | B2 |  |  | B1 |  |
| Finger 1: | GTG | R | S | D | A | L | T | R* | SEQ ID NO: 26 |
|  |  | R | S | N | S | L | T | R  | SEQ ID NO: 27 |
| Finger 2: | AAG | R | S | D | T | L | S | N  | SEQ ID NO: 28 |
|  |  | R | K | D | N | L | K | N  | SEQ ID NO: 29 |
|  |  | R | S | S | M | L | T | Q* | SEQ ID NO: 30 |
| Finger 3: | GGC | D | R | S | H | L | A | R* | SEQ ID NO: 31 |
|  |  | E | S | N | H | L | T | R  | SEQ ID NO: 32 |
|  |  | E | R | S | K | L | A | R  | SEQ ID NO: 33 |
|  |  | D | P | G | H | L | V | R  | SEQ ID NO: 34 |

Structure of CMV-HBGZF1

| CMV | ATG-NLS-FLAG-Finger 1{RSDALTR}-Finger2{RSSNLTQ}-Finger3{DRSHLAR}-Fn |
|---|---|

SEQ ID NO: 26    SEQ ID NO: 30    SEQ ID NO: 31

Fig. 7

Design of HCGCZF2

Target Binding Site: 5' GGG GGA GCA 3'    SEQ ID NO: 38

F3   F2   F1

|  |  | -1 | 1 | 2 | 3 | 4 | 5 | 6 |  |
|---|---|---|---|---|---|---|---|---|---|
|  |  | B3 |  | B2 |  |  |  | B1 |  |
| Finger 1: | GCA | Q | S | G | S | L | T | R | SEQ ID NO: 39 |
|  |  | Q | S | G | D | L | T | R | SEQ ID NO: 40 |
|  |  | Q | S | G | D | L | T | R | SEQ ID NO: 41 |
|  |  | Q | S | N | D | L | T | R* | SEQ ID NO: 42 |
| Finger 2: | GGA | Q | S | G | H | L | Q | K | SEQ ID NO: 43 |
|  |  | Q | R | A | H | L | E | R | SEQ ID NO: 44 |
|  |  | Q | S | S | H | L | T | R* | SEQ ID NO: 45 |
| Finger 3: | GGG | R | S | D | H | L | A | R | SEQ ID NO: 46 |
|  |  | R | S | D | H | L | T | R | SEQ ID NO: 47 |
|  |  | R | S | S | H | L | T | R* | SEQ ID NO: 48 |

Structure of CMV-HCGCZF2

| CMV | ATG-NLS-FLAG-Finger 1(QSNDLTR)-Finger 2(QSSHLTR)-Finger 3(RSSHLTR)-Fn |

SEQ ID NO: 42      SEQ ID NO: 45      SEQ ID NO: 48

Fig. 10

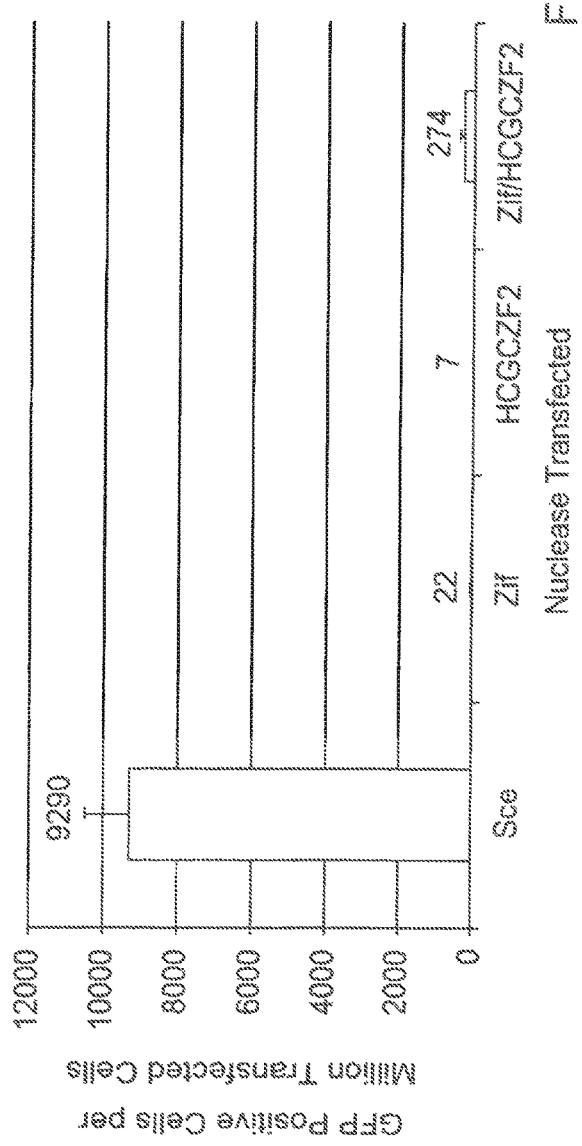

SEQ ID NO: 50
5' acC atC ttC ttcaag Gac Gac Ggc aac stop-Sce site tac
3' tgG taG aaG aag ttc Cgc Ctg Ccg ttc Fn — GFPCN2
GFPCN1 — Fn SEQ ID NO: 51
bp 441 5' acc ggCgcCcaC catcgc GtcG caGcc ctg 3' bp 471
SEQ ID NO: 52 tgg ccG cg Ggtg gtagcg CagCgtCgg gac
                    CD8ZF1  Fn      CD8ZF2

Fig. 13A

USE OF CHIMERIC NUCLEASES TO STIMULATE GENE TARGETING

CROSS-REFERENCE TO RELATED APPLICATIONS

This application is a continuation of U.S. patent Ser. No. 10/656,531 filed Sep. 5, 2003, now U.S. Pat. No. 9,447,434, which claims the benefit of U.S. Provisional Application Nos. 60/408,454 filed on Sep. 5, 2002, 60/419,341 filed on Oct. 17, 2002 and 60/484,788 filed on Jul. 3, 2003, the disclosures of which are hereby incorporated by reference in their entireties.

FUNDING

This invention was made with government support under Grant No. HL70268-01 and under Grant No. ROI-GM39458 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 27, 2016, is named 8325-0150_01_SL.TXT and is 13,756 bytes in size.

BACKGROUND OF THE INVENTION

Gene targeting is a technique to introduce genetic change into specific locations in the genome of a cell. The targeted introduction of genetic changes can be used as a powerful experimental approach and as a therapeutic technique for ameliorating genetic aspects of disease. Gene targeting is widely used in murine embryonic stem cells (ES cells) and certain other specialized cell types such as chicken B-cell line DT40 to facilitate research on the genetic control of many processes. Gene targeting also represents a potentially powerful way of performing gene therapy. More than 3,000 diseases are caused by mutations such as, for example, hemophilia, Tay-Sachs disease, Duchenne's muscular dystrophy, Huntington's disease, alpha-thalassemia, Lesch Nyhan syndrome, etc. Most of these diseases cannot be treated medically. If gene targeting could be harnessed for use in humans, it could be used to correct many of these genetic diseases.

It is known that genes introduced into mammalian cells integrate into the DNA of the cell primarily at non-homologous sites. Thus, instead of replacing a mutated gene, the wild type copy will be introduced at another locus in the DNA. In the cell types that have been used for gene therapy, the rate of gene targeting is extremely low. Therefore, there is a need to develop a technique to increase the efficiency of gene targeting so that it can be used in cell types for experimental and therapeutic purposes including gene therapy.

SUMMARY OF THE INVENTION

The present invention is based in part on the discovery of methods and compositions for gene targeting in cells, and particularly in mammalian cells. Methods and compositions disclosed herein may be used, for example, to alter one or more selected sequences in the genome of a cell. An alteration may include a deletion, an insertion (possibly of an entire gene) or a change in one or more basepairs, as well as combinations of several different changes. An alteration may be made to effect a variety of possible purposes, including, for example, to ameliorate a genetic disorder in a subject, to confer a desirable genotype on a subject or cell, to increase the production or activity of a beneficial polypeptide in a subject or cell, to decrease the production or activity of an undesirable polypeptide in a subject or cell and to investigate the effects of genetic changes in a non-human organism or any cell type.

In certain embodiments, the present invention provides methods for changing a target sequence in genomic DNA of a cell, such as a mammalian cell. Such method may comprise: (a) introducing a chimeric nuclease into the cell, wherein said chimeric nuclease comprises: (i) a DNA binding domain; and (ii) a cleavage domain; and (b) introducing a repair substrate into the cell, wherein said repair substrate comprises: (i) a nucleic acid sequence that is substantially identical to regions on one or both sides of the target sequence; and (ii) a nucleic acid sequence which changes the target sequence upon recombination between the repair substrate and the target sequence, whereby the target sequence is changed by the repair substrate upon recombination. Optionally, the target sequence is selected such that it contains an allele that contributes to a disease, such as a genetic disease, so that the target sequence is repaired by the repair substrate. However, methods disclosed herein may also be used to introduce essentially any desirable change in genomic sequence, including the introduction of novel sequences, such as transgenes for expression, the inactivation or attenuation of a gene, and the introduction of a sequence change that confers an improved phenotype. In certain embodiments, the cell is an in vitro cell. Preferably, the cell is a human cell.

In certain specific embodiments, a target sequence is modified by a repair substrate in the subject method. For example, an allele in the target sequence that contributes to a disease in the target sequence may be repaired by a repair substrate. In another embodiment, a target sequence is attenuated or inactivated by a repair substrate in the subject method. For example, the target sequence may be situated in a portion of a gene, and the alteration of the sequence decreases gene expression or decreases the activity or stability of the gene product. In yet another specific embodiment, a target sequence is replaced by, or has inserted within it, a heterologous sequence (in the repair substrate) in the subject method. For example, the heterologous sequence may be a transgene intended for expression in the cell. The alteration may be in the form of an insertion, deletion, or change in the sequence, or a mixture thereof. Optionally, the chimeric nuclease and the repair substrate of the method are encoded by a single vector introduced into the cell. In another specific embodiment, the chimeric nuclease of the method further comprises a nuclear localization signal (NLS).

In certain cases, the repair substrate of the method is operably linked to a promoter in a vector. In certain cases, the chimeric nuclease of the method can be introduced into the cell by introducing a nucleic acid encoding the chimeric nuclease. Optionally, this nucleic acid is operably linked to a promoter. Preferably, such promoters are inducible promoters. Optionally, the vector is a viral vector and may be a vector designed for introduction into an individual. In particular embodiments, the subject methods contemplate introducing into the cell either the chimeric nuclease protein or a nucleic acid encoding the chimeric nuclease.

In certain cases, the DNA binding domain of the chimeric nuclease comprises a zinc finger domain. In particular, the DNA binding domain of the chimeric nuclease may comprise two, three or more zinc finger domains. In other cases, the cleavage domain of the chimeric nuclease comprises a cleavage domain of a restriction endonuclease such as a cleavage domain of a type IIs restriction endonuclease (e.g., a FokI cleavage domain). Optionally, the chimeric nuclease of the method may either form a homodimer of two identical chimeric nucleases or form a heterodimer of two different chimeric nucleases. In a particular embodiment, methods of the invention contemplate use of a nucleic acid that further encodes a second chimeric nuclease, wherein the second chimeric nuclease forms a heterodimer with said chimeric nuclease.

In certain embodiments, the subject methods may be used to alter a genomic target sequence that renders a subject susceptible to an infectious disease. For example, many viral and bacterial pathogens enter a cell by binding to and recruiting a set of cell surface and intracellular proteins. Gene targeting may be used to eliminate or attenuate such a binding site or entry mechanism. An exemplary target gene is the CCR5 gene that participates in HIV entry into T cells. Cells of an individual who is infected with HIV or susceptible to HIV infection may be treated so as to decrease the ability of HIV to enter the cells. For example, the cell may be a T cell or a T cell progenitor such as a hematopoietic stem cell.

In still another embodiment, the subject methods may be used to introduce a transgene for expression in the cell. For example, a genetic disease caused by a decrease in the level of a necessary gene product may be treated or ameliorated by providing a transgene expressing the needed gene product. The transgene may be targeted to the location of the endogenous gene, or to a different location. In a particular embodiment of the subject method, the site of interest is a transcriptionally active location, or an "open location" in chromosome. The term "open location," as used herein, refers to a specific chromosomal location that is known to support transcription.

In yet another embodiment, the present invention provides methods for ameliorating, treating or preventing a disease in an individual, wherein the disease is caused in part or in whole by a genomic target sequence. Such methods may comprise: (a) introducing a chimeric nuclease into a cell, wherein said chimeric nuclease comprises: (i) a DNA binding domain; and (ii) a cleavage domain; and (b) introducing a repair substrate into the cell under conditions appropriate for introducing the repair substrate into the site of interest, wherein said repair substrate comprises: (i) a nucleic acid sequence that is substantially identical to one or more regions proximal to or flanking a target sequence in chromosomal DNA; and (ii) a nucleic acid sequence which replaces the target sequence upon recombination between the repair substrate and the target sequence, whereby the genetic disease is ameliorated, treated or prevented. Preferably, the individual is a human. In certain embodiments, the chimeric nuclease further comprises a nuclear localization signal (NLS).

In certain embodiments, the cell of the method is an in vitro cell obtained from the individual. By "obtained" is meant that that the cell of the method may be a cell that is literally taken from the individual or a cell that derives therefrom, through mitotic division, cell fusion, cell differentiation or the like. Optionally, the method may further comprise reintroducing to the individual the cell that has been treated with the chimeric nuclease and the repair substrate. In certain cases, the cell is a stem cell or a population of cells comprising the stem cell.

In particular embodiments of the subject method, a genetic disease is selected from the group consisting of severe combined immunodeficiency (SCID), sickle cell disease, and hemophilia.

In another specific embodiment, the cell of the method is an in vitro cell obtained from a donor. Optionally, the method may further comprise reintroducing to the individual the cell that has been treated with the chimeric nuclease and the repair substrate. In certain cases, the cell is a stem cell or a population of cells comprising the stem cell.

In another embodiment, the cell of the method is an in vivo cell in the individual. Optionally, a nucleic acid encoding the chimeric nuclease and the repair substrate are introduced directly to a target tissue comprising the cell.

In an embodiment of the subject method, the chimeric nuclease and the repair substrate are encoded by a single vector introduced into the cell.

In certain cases, the repair substrate of the method is operably linked to a promoter in a vector. In certain cases, the chimeric nuclease of the method can be introduced into the cell by introducing a nucleic acid encoding the chimeric nuclease. Optionally, this nucleic acid is operably linked to a promoter. Preferably, such promoters are inducible promoters. Optionally, the vector is a viral vector. In particular embodiments, the subject methods contemplate introducing into the cell either the chimeric nuclease protein or a nucleic acid encoding the chimeric nuclease.

In certain cases, the DNA binding domain of the chimeric nuclease comprises a zinc finger domain. In particular, the DNA binding domain of the chimeric nuclease may comprise two, three or more zinc finger domains. In other cases, the cleavage domain of the chimeric nuclease comprises a cleavage domain of a restriction endonuclease such as a FokI cleavage domain. Optionally, the chimeric nuclease of the method may either form a homodimer of two identical chimeric nucleases or form a heterodimer of two different chimeric nucleases. In a particular embodiment, methods of the invention contemplate use of a nucleic acid that further encodes a second chimeric nuclease, wherein the second chimeric nuclease forms a heterodimer with said chimeric nuclease.

In still another embodiment, the present invention provides methods of designing a chimeric nuclease or a nucleic acid encoding a chimeric nuclease. Such methods may comprise: (a) selecting a mammalian target sequence for gene targeting; (b) identifying a possible DNA binding sequence within workable proximity of the target sequence (including possible binding sites within the target sequence); (c) designing a DNA binding domain that binds to the DNA binding sequence identified in (b); and (d) coupling the DNA binding domain in (c) to a cleavage domain to make a chimeric nuclease. Optionally, the coupling may be achieved by generating a nucleic acid encoding a fusion protein comprising the DNA binding domain and the cleavage domain. In certain embodiments, the subject method further comprises coupling a nuclear localization signal (NLS) to the chimeric nuclease.

In certain cases, the DNA binding domain of the chimeric nuclease comprises a zinc finger domain. The DNA binding domain of the chimeric nuclease may comprise three or more zinc finger domains. In other cases, the cleavage domain of the chimeric nuclease comprises a cleavage domain of a restriction endonuclease such as a FokI cleavage domain. Optionally, the chimeric nuclease of the method may either form a homodimer of two identical chimeric nucleases or form a heterodimer of two different chimeric nucleases. In particular embodiments, methods of the invention contemplate use of a nucleic acid that further encodes a second chimeric nuclease, wherein the second chimeric nuclease forms a heterodimer with said chimeric nuclease.

In a specific embodiment, the subject method further comprises testing the chimeric enzyme for toxicity in a cell. In another specific embodiment, the subject method further comprises testing the cleavage site specificity of the chimeric enzyme.

In certain aspects, novel chimeric nucleases are disclosed herein, as well as complexes comprising two or more chimeric nucleases. In certain embodiments, the invention provides chimeric nucleases comprising: (i) a DNA binding domain; (ii) a cleavage domain; and (iii) a nuclear localization signal. Optionally, a chimeric nuclease includes a DNA binding domain that binds to a recognition sequence comprising at least 3, 6, 9 or more designated nucleotides. Optionally, the DNA binding domain of a chimeric nuclease comprises at least one, two, three or more zinc finger domains. The cleavage domain of a chimeric nuclease may comprise a cleavage domain of a type IIs restriction endonuclease, such as a FokI cleavage domain. An example of a preferred type of chimeric nuclease is a chimeric nuclease comprising a nuclear localization signal, a DNA binding domain comprising three zinc finger domains and recognizing a recognition sequence comprising 9 designated nucleotides, and further comprising a cleavage domain of a FokI restriction endonuclease.

In certain embodiments, the disclosure provides a chimeric nuclease comprising: (a) a cleavage domain; and (b) a DNA binding domain comprising at least three zinc fingers, wherein the DNA binding domain binds to a recognition sequence that occurs at a position in a mammalian genome within at least 500 base pairs, and preferably within at least 200 or 100 base pairs, of an allele that contributes to a genetic disorder, and wherein the recognition sequence comprises at least 9 nucleotides.

In certain aspects, the disclosure relates to the discovery that conjointly acting chimeric nucleases may be used advantageously in gene targeting. Accordingly, in certain aspects, the disclosure provides complexes comprising a first chimeric nuclease and a second chimeric nuclease, wherein the first and second chimeric nuclease act conjointly to facilitate gene targeting. Optionally, the first and second chimeric nuclease are identical. In certain embodiments, one or both of the first and second chimeric nucleases comprise a nuclear localization signal.

In certain aspects, the invention provides nucleic acids encoding any of the chimeric nucleases disclosed herein, and vectors comprising such nucleic acids. Vector may be designed, for example, for use with in vitro cells or for introduction into cells that are part of an organism. In certain embodiments, the present invention provides a vector that comprises: a nucleic acid encoding a chimeric nuclease and a nucleic acid encoding a repair substrate, wherein the chimeric nuclease comprises: (i) a DNA binding domain; and (ii) a cleavage domain; and wherein the repair substrate comprises: (i) a nucleic acid sequence that is substantially identical to a region proximal to or flanking a target sequence in chromosomal DNA; and (ii) a nucleic acid sequence which replaces the target sequence upon recombination between the repair substrate and the target sequence.

In certain cases, the repair substrate in the vector is operably linked to a promoter. Similarly, the chimeric nuclease in the vector can be encoded by a nucleic acid that is operably linked to a promoter. Preferably, the promoter is an inducible promoter. Optionally, the vector is a viral vector.

In a further embodiment, the vector of the present invention comprises both a nucleic acid encoding the chimeric nuclease and a nucleic acid comprising the repair substrate.

In another embodiment, the chimeric nuclease encoded in the vector further comprises a nuclear localization signal (NLS).

In certain aspects, the present invention provides cells comprising any of the chimeric nuclease proteins, encoding nucleic acids and vectors disclosed herein. In certain embodiments, a mammalian cell comprising a nuclease, such as a chimeric nuclease, and a repair substrate. A chimeric nuclease comprises: (i) a DNA binding domain; and (ii) a cleavage domain. A repair substrate comprises: (i) a nucleic acid sequence that is substantially identical to a region proximal to or flanking a target sequence in chromosomal DNA; and (ii) a nucleic acid sequence which replaces the target sequence upon recombination between the repair substrate and the target sequence. Optionally, the target sequence in chromosomal DNA includes a mutation. In certain embodiments, the mammalian cell is an in vitro cell. Preferably, the mammalian cell is a human cell. In certain embodiments, a mammalian cell comprises a chimeric nuclease and a repair substrate for a relatively brief period of time, and preferably for a period of time that is sufficient to effect the desired genetic change yet not so long as to compromise the viability of the cell.

In certain cases, the repair substrate in the mammalian cell is operably linked to a promoter in a vector. Similarly, the chimeric nuclease in the mammalian cell can be encoded by a nucleic acid that is operably linked to a promoter in a vector. Preferably, the promoters are inducible promoters, although other promoters may also be used. Optionally, the vector is a viral vector.

In certain embodiments, a mammalian cell of the present invention comprises a vector that comprises both a nucleic acid encoding a chimeric nuclease and a nucleic acid encoding a repair substrate.

In another embodiment, a chimeric nuclease in a mammalian cell comprises a nuclear localization signal (NLS).

In another embodiment, the present invention provides a mammalian cell comprising nucleic acids that encode a chimeric nuclease and a repair substrate, wherein the chimeric nuclease comprises: (i) a DNA binding domain; and (ii) a cleavage domain, and wherein the repair substrate comprises: (i) a nucleic acid sequence that is substantially identical to a region proximal to or flanking a target sequence in chromosomal DNA; and (ii) a nucleic acid sequence which replaces the target sequence upon recombination between the repair substrate and the target sequence.

In another embodiment, the present invention provides a nucleic acid encoding a chimeric nuclease, wherein the chimeric nuclease comprises: (i) a DNA binding domain; (ii) a cleavage domain; and (iii) a nuclear localization signal (NLS). In a specific embodiment, the present invention provides a vector comprising such a nucleic acid. In certain cases, the nucleic acid encoding the chimeric nuclease is operably linked to a promoter for expression in a mammalian cell. Preferably, the promoter is an inducible promoter. Optionally, the vector is a viral vector.

In certain cases, the DNA binding domain of the chimeric nuclease of the claimed vector comprises a zinc finger domain. In particular, the DNA binding domain of the chimeric nuclease may comprise two, three or more zinc finger domains. In other cases, the cleavage domain of the chimeric nuclease comprises a cleavage domain of a restriction endonuclease such as a FokI cleavage domain. Optionally, the chimeric nuclease in the vector may either form a homodimer of two identical chimeric nucleases or form a heterodimer of two different chimeric nucleases. In a particular embodiment, the vector of the invention may further comprise a nucleic acid encoding a second chimeric nuclease, wherein the second chimeric nuclease forms a heterodimer with said chimeric nuclease.

In another embodiment, the present invention provides an in vitro mammalian cell. Such mammalian cell comprises a nucleic acid vector disclosed herein which encodes a chimeric nuclease. The chimeric nuclease comprises: (i) a DNA binding domain; (ii) a cleavage domain; and (iii) a nuclear localization signal (NLS). Preferably, the in vitro mammalian cell is a human cell.

In another embodiment, the present invention provides an in vitro mammalian cell. Such mammalian cell comprises the above claimed nucleic acid vectors comprising a nucleic acid encoding a chimeric nuclease and a nucleic acid encoding a repair substrate, wherein the chimeric nuclease comprises: (i) a DNA binding domain; and (ii) a cleavage domain; and wherein the repair substrate comprises: (i) a nucleic acid sequence that is substantially identical to a region proximal to or flanking a target sequence in chromosomal DNA; and (ii) a nucleic acid sequence which replaces the target sequence upon recombination between the repair substrate and the target sequence. Preferably, the in vitro mammalian cell is a human cell.

In another embodiment, the present invention provides a recombinant transfection system. Such transfection system comprises: (i) one of the above claimed vectors; and (ii) a gene delivery composition for delivering said vector to a cell and causing said cell to be transfected with said vector. In a specific embodiment, the gene delivery composition is selected from the group consisting of: a recombinant viral particle, a liposome, and a poly-cationic nucleic acid binding agent.

In certain embodiments, the invention provides methods for operating a gene targeting service business. Such a method may involve, for example, receiving a customer request for a chimeric nuclease and/or a repair substrate in order to effect a change in a particular gene or genomic region. Upon receipt of the request, the service provider may identify sequences in the targeted region that are amenable to recognition by a chimeric nuclease, design a nucleic acid encoding the appropriate nuclease and transmit to the customer any or all of: the chimeric nuclease, the encoding nucleic acid (preferably in an expression vector) and the sequence of the encoding nucleic acid. Likewise, the service provider may design and create a repair substrate for a customer. Optionally, a method may include performing one or more test gene targeting trials to select an effective chimeric nuclease and/or repair substrate. Optionally, the service provider may perform the gene targeting and provide the altered cells or whole organisms comprising one or more altered cells to the customer.

In certain embodiments, the invention provides kits for gene targeting. A kit may comprise a repair substrate cassette vector, the vector comprising one, two or more marker genes (e.g., selectable markers such as a puromycin resistance gene) flanked by restriction enzyme recognition sites or other sites that facilitate cloning (e.g., sites that are acted on by a recombinase, topoisomerase or integrase). A kit may also comprise a chimeric nuclease cassette vector, the vector comprising a gene for a nuclease comprising discrete and separately modifiable nuclease and recognition domains. Optionally, the recognition domains are engineered to contain restriction enzyme recognition sites (preferably ones that minimally affect the amino acid sequence) to facilitate the swapping of recognition domains. A kit may comprise detailed instructions explaining how to construct a suitable chimeric nuclease and/or how to perform gene targeting.

The embodiments and practices of the present invention, other embodiments, and their features and characteristics, will be apparent from the description, figures and claims that follow.

BRIEF DESCRIPTION OF THE DRAWINGS

FIGS. 1A through 1D show a green fluorescent protein (GFP) gene targeting system.

FIG. 1A illustrates a GFP gene targeting system. The artificial gene target (A658, top line) consisted of a GFP gene mutated by a 35 basepair insertion which includes a stop codon and a recognition site for the I-SceI endonuclease (Sce) (5' TAGGGATAACAGGGTAAT 3', SEQ ID NO: 1) at basepair 327 of the coding sequence. The GFP gene was driven by a hybrid cytomegalovirus enhancer/chicken β3-actin promoter ("CMV/CBA" or "CBA"). The GFP gene was part of bicistronic transcript in which an internal ribosomal entry site ("IRES") allowed translation of the human CD8α gene ("CD8"). The bicistronic message contained a Woodchuck post-trancriptional regulatory element ("WPRE") to increase messenger RNA levels (Zufferey et al., 1999, J Virol, 73:2886-92). Finally, the locus contained a gene with the phosphoglycerate kinase promoter ("PGK") driving the neomycin phosphotransferase gene (NEO) to allow selection by the antibiotic G418. The repair substrates RS2100 (middle line) and RS2700 (bottom line) are also depicted. They consisted of a GFP gene that has been truncated at basepair 37 of the coding sequence and thus were missing the initiation codon ("truncGFP"). The truncated GFP gene was followed by the IRES-CD8 for RS2100 or IRES-CD8-WPRE for RS2700 as in A658. The A658 gene target was introduced into 293 cells by electroporating $2\times10^6$ cells with 10 μg of supercoiled A658 plasmid DNA. Cells were selected in 500 .mu.g/ml G418 for two weeks. Monoclonal cell lines were made by picking individual colonies and identifying those with high surface CD8 expression by staining with phycoerythrin-conjugated anti-CD8 antibody (BD Biosciences, San Jose, Calif.) (293 cells normally do not express CD8). Polyclonal cell lines were made by purifying a population of cells using Miltenyi anti-CD8 microbeads and a MACS minicolumn (Miltenyi Biotec, Auburn, Calif.). Gene targeting was measured by transfecting 293/A658 cells with RS2100 with or without a Sce expression plasmid along with a control plasmid (pON405) to determine the transfection efficiency. Applicants used three different promoters to drive Sce expression: PGK, cytomegalovirus ("CMV"), and CBA. The cells were then incubated for 3 days and the percentage of GFP positive cells measured by flow cytometry using a FACScan (BD Biosciences, San Jose, Calif.). The gene targeting rate was determined by normalizing the measured percentage of GFP positive cells to the transfection efficiency.

FIG. 1B shows representative flow cytometry plots of gene targeting. GFP positive cells were quantitated in region "R2" as depicted in the right flow plot. It shows 293/A658 cells after transfection with Sce expression plasmid alone. There are no GFP positive cells. The left plot, "S-GT," shows 293/A658 cells after transfection with RS2100 alone. The two GFP positive cells are circled and represent spontaneous gene targeting events. The middle plot, "DSB-GT,"

shows 293/A658 cells after co-transfection with RS2100 and CBA-Sce. In this plot there are numerous GFP positive cells in region R2.

FIG. 1C shows gene targeting rates in 293 Cells. The results are shown as both the number of gene targeting events per million transfected cells ("Events/$10^6$ cells") plus/minus one standard deviation and as an overall rate. The results are shown for four different gene targets. In the "1 bp insertion" target ($2^{nd}$ column), a nonsense mutation was created in the GFP gene at bp 321 of the coding region that abrogates functional GFP expression. For the "7 bp insertion" target ($3^{rd}$ column), a 7 bp sequence was inserted at bp 327 of the GFP coding region. The gene target for the "35 bp insertion" ($4^{th}$ and $5^{th}$ columns) was A658 and the target for the "66 bp insertion" ($6^{th}$ column) was QQR8 (schematized in FIG. 3A). The row labeled "Sce" shows whether Sce was co-transfected or not. The $7^{th}$ column labeled "Fold Stimulation by Sce Induced DSB" was the stimulation of the gene targeting rate on target A658 induced by expression of Sce.

FIG. 1D shows time course of gene targeting. The relative rate of DSB-GT was normalized to day 3.

FIGS. 2A through 2E show parameters regulating the rate of DSB-induced gene targeting. In these experiments, transfections were performed by the calcium phosphate technique in 24-well plates. In FIGS. 2A through 2D, the rates of gene targeting were normalized to the standard conditions of using 200 ng of RS2100 and 200 ng of PGK-Sce. In experiments where the amount of a transfected component was varied, the total DNA amount was kept constant by adding pBSK(−) plasmid (Stratagene, La Jolla, Calif.).

Figures 2A, 2B:
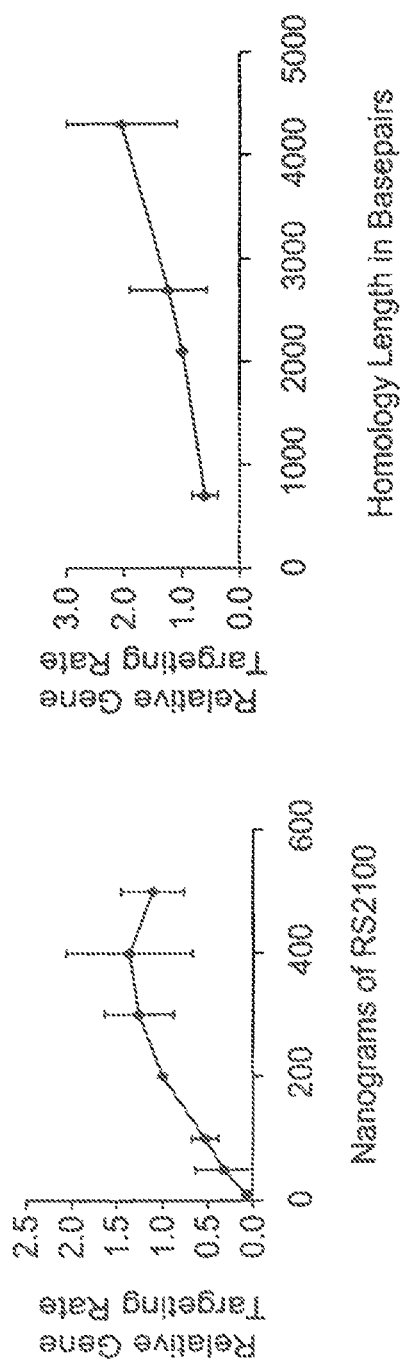

FIG. 2A shows gene targeting rate vs. substrate amount. The results were normalized to the rate of gene targeting obtained after transfecting 200 nanograms (ng) of RS2100.

FIG. 2B shows gene targeting rate vs. homology length. The results were normalized to the rate obtained with plasmid RS2100. The plasmid with 800 bp of homology (RS800) was missing the IRES-CD8 component of RS2100. The plasmid with 2700 bp of homology (RS2700) is depicted in FIG. 1A. The plasmid with 4200 bp of homology (RS4200) had the addition of both the WPRE and the PGK-NEO components to the 3' end of RS2100. A constant amount (200 ng) of each repair substrate was transfected but the relative rate of DSB-GT was normalized to the molar amount transfected.

FIG. 2C shows gene targeting rate vs. amount of Sce expression plasmid transfected. The results were normalized to the rate of gene targeting obtained when 200 ng of PGK-Sce was transfected.

FIG. 2D shows gene targeting rate vs. transcriptional status of repair substrate. "Untranscribed" was the rate of DSB-GT using RS2100. "Transcribed" was the rate of DSB-GT when the sense strand of RS2100 was transcribed using the CMV promoter (CMV-RS2100). The rates were normalized to the rate of gene targeting obtained using RS2100.

FIG. 2E shows optimization of gene targeting. Columns labeled "1" are when Sce and RS2100 are on the same plasmid and columns labeled "2" are when Sce and RS2100 are on separate plasmids. 30,000 GFP positive cells per million transfected cells is equivalent to a gene targeting rate of 3%.

FIGS. 3A through 3D show gene targeting induced by chimeric nucleases. In each of the experiments the rate of gene targeting was measured by co-transfecting the appropriate nuclease with the repair substrate RS2700 (FIG. 1A).

FIG. 3A shows schematics of the chimeric nucleases and chimeric nuclease targets. The gene targets (left panel) were identical to A658 except that additional sequence, which expands the insertion, have been inserted into the GFP gene adjacent to the Sce recognition site ("Sce site"). In QQR8 (top line of left panel) and QQR6 (middle line of left panel) inverted repeats of the binding site ("QQR site") for the QQR zinc finger triplet (5' GGGGAAGAA 3', SEQ ID NO: 2) were inserted with either a 6 bp, "6," (QQR6) or 8 bp spacer, "8," (QQR8). In QQRZIF6 (bottom line of left panel), a binding site for the Zif268 triplet finger ("Zif Site") (5' GCGTGGTCG 3', SEQ ID NO: 3) was inserted in an inverted orientation to a QQR site with a 6 bp spacer ("6") between the sites. Polyclonal 293 cell lines were made from QQR8, QQR6, and QQRZIF6 as described in FIG. 1. The chimeric nucleases (shown in right panel) were driven by the CMV promoter, "CMV." Each have a standard initiation codon "ATG" followed by a nuclear localization signal, "N," at the amino-terminus. The triplet zinc finger domain, either "QQR" for the QQR zinc finger triplet (Shi et al., 1995, Science, 268:282-284) or "Zif" for the Zif268 triplet (Wolfe et al., 2001, Structure (Camb), 9:717-23) follow the nuclear localization signal. There is then a variable amino acid linker, 18 amino acids ("L18") in CMV-QQR-L18-Fn (top line of right panel), zero amino acids ("L0") in CMV-QQR-L0-Fn (middle line of right panel), or three amino acids ("L3") in CMV-ZIF-L3-Fn (bottom line of right panel) before the endonuclease domain of the FokI restriction enzyme ("Nuclease" or "Fn") (Chandrasegaran et al., 1999, Biol Chem, 380:841-8). CMV-QQR-L18-Fn and CMV-QQR-L0-Fn were cloned from previously characterized fusion proteins (Smith et al., 2000, Nucleic Acids Res, 28:3361-9) while CMV-ZIF-L3-Fn is novel.

FIG. 3B shows gene targeting using chimeric nuclease homodimers.

FIG. 3C shows gene targeting with chimeric nuclease heterodimers.

FIG. 3D shows time course of gene targeting using chimeric nucleases.

FIG. 4 (SEQ ID NO: 16) demonstrates the sequence of the human β-globin gene surrounding the codon mutated to cause sickle cell anemia. Depicted are two pairs of potential chimeric nucleases (HBGZF1 and HBGZF2; HBGZF3 and HBGZF4). The binding sites for the chimeric nucleases are highlighted by being in capital letters.

FIG. 5 demonstrates the binding site for HBGZF1 (SEQ ID NO: 17) and the zinc finger domains (SEQ ID NOs: 18 to 23) that recognize each triplet using the single letter code (top line). The bottom line is a schematic depicting the structure of the CMV-HBGZ1 construct.

Figure 6:
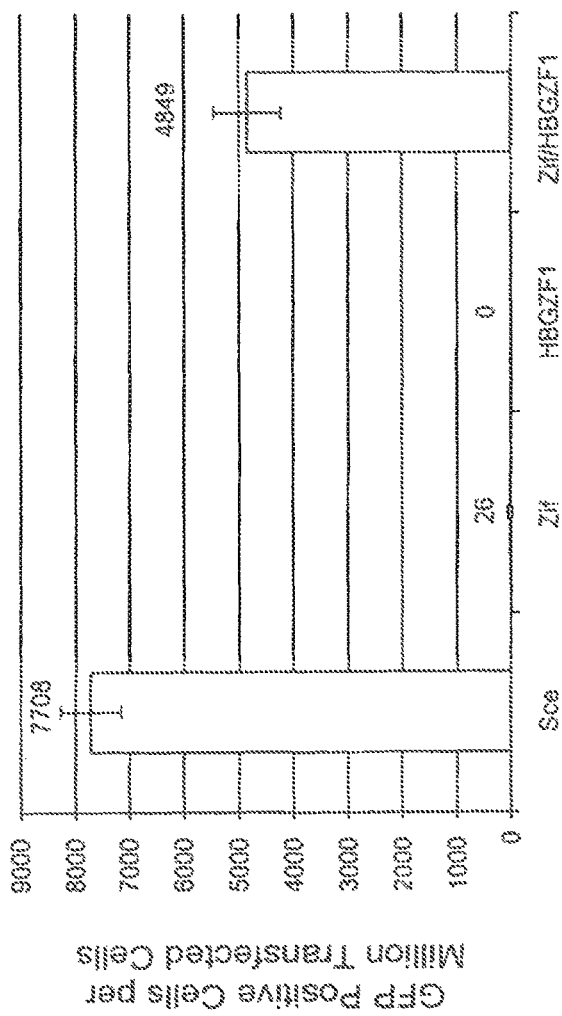

FIG. 6 shows the results (graph of bottom panel) of gene targeting with HBGZF1 and the GFP gene target (SEQ ID NO: 24) containing the artificial hybrid HBGZF1/Zif268 binding site shown in the top panel.

FIG. 7 shows the design and target site for HBGZF4 (SEQ ID NO: 25) and the zinc finger domains (SEQ ID NOs: 26 to 34) that recognize each triplet using the single letter code (top panel). The bottom panel is a schematic depicting the structure of the CMV-HBGZ4 construct.

Figure 8:
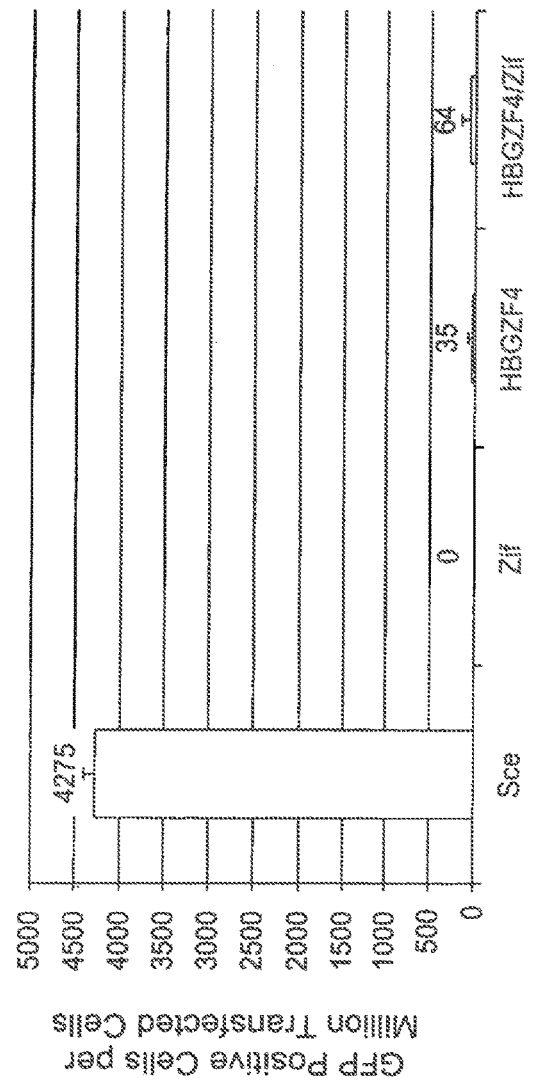

FIG. 8 shows the results (graph of bottom panel) of gene targeting with HBGZF4 and the GFP gene target (SEQ ID NO: 35) containing the artificial hybrid HBGZF4/Zif268 binding site shown in the top panel.

Figures 9A, 9B:
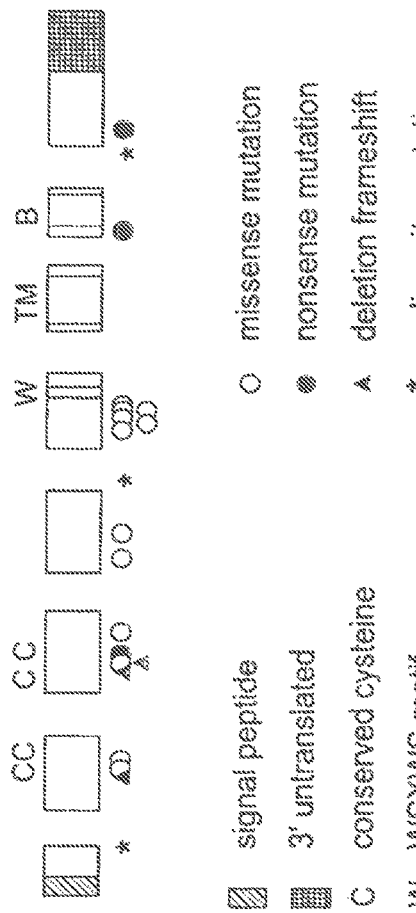

FIG. 9A shows the structure of the human common γ-chain and the location of mutations in the gene that lead to SCID, derived from Notarangelo et al, 2002. FIG. 9B (SEQ ID NOs: 36 and 37) shows the sequence of exon 5 and the proposed binding sites for chimeric nucleases HCGCZF1 and HCGCZF2.

FIG. 10 shows the binding site for HCGCZF2 (SEQ ID NO: 38) and the structure of HCGCZF2 using the amino acids for zinc fingers 1-3 (SEQ ID NOs: 39 to 48) deduced from the zinc-finger code from Sera and Uranga (2002) (top panel). The bottom panel is a schematic depicting the structure of the CMV-HBGCZ2 construct.

FIG. 11 shows the results (graph of bottom panel) of gene targeting with HBGZF2 and the GFP gene target (SEQ ID NO: 49 shown in top panel) containing the artificial hybrid HCGCZF2/Zif268 binding site.

Figure 12A:
Figure 12B:
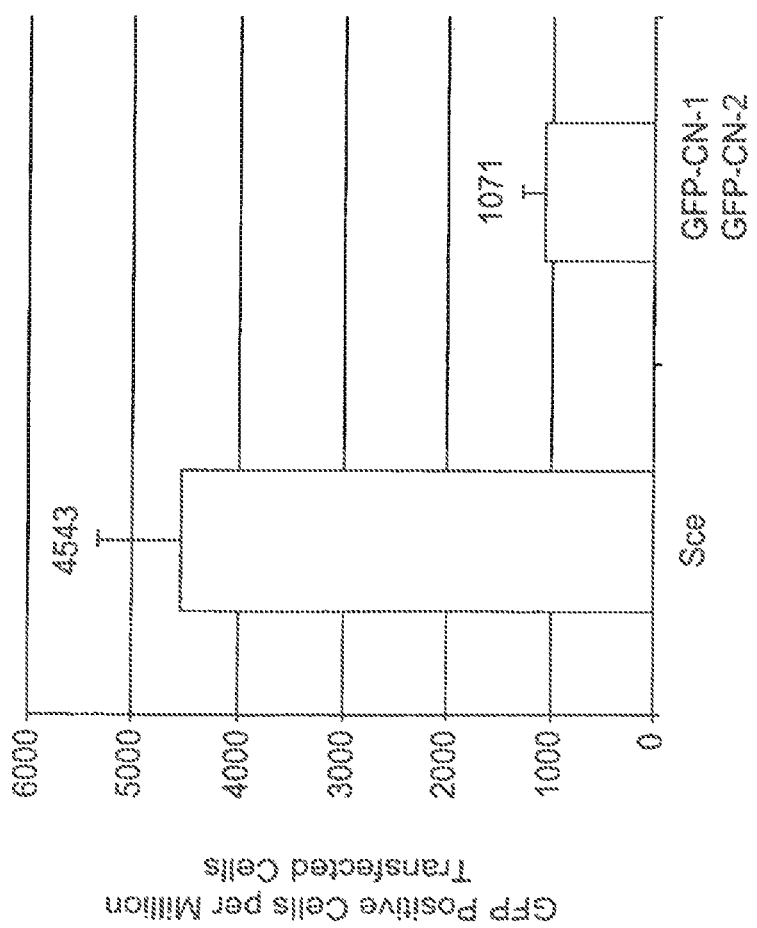

FIGS. 12A and 12B show Gene Targeting with GFP chimeric nucleases. FIG. 12A shows the sequence of the target sequence in GFP gene (SEQ ID NO: 50) and a schematic representation of chimeric nucleases designed to cleave the GFP gene. The GFP chimeric nuclease target site lies just 5' to the insertion of the I-SceI recognition site ("Sce site"). FIG. 12B shows the rate of gene targeting in 293 cells after co-transfection of the indicated nuclease with the repair substrate A767 described in example 1.

Figure 13B:
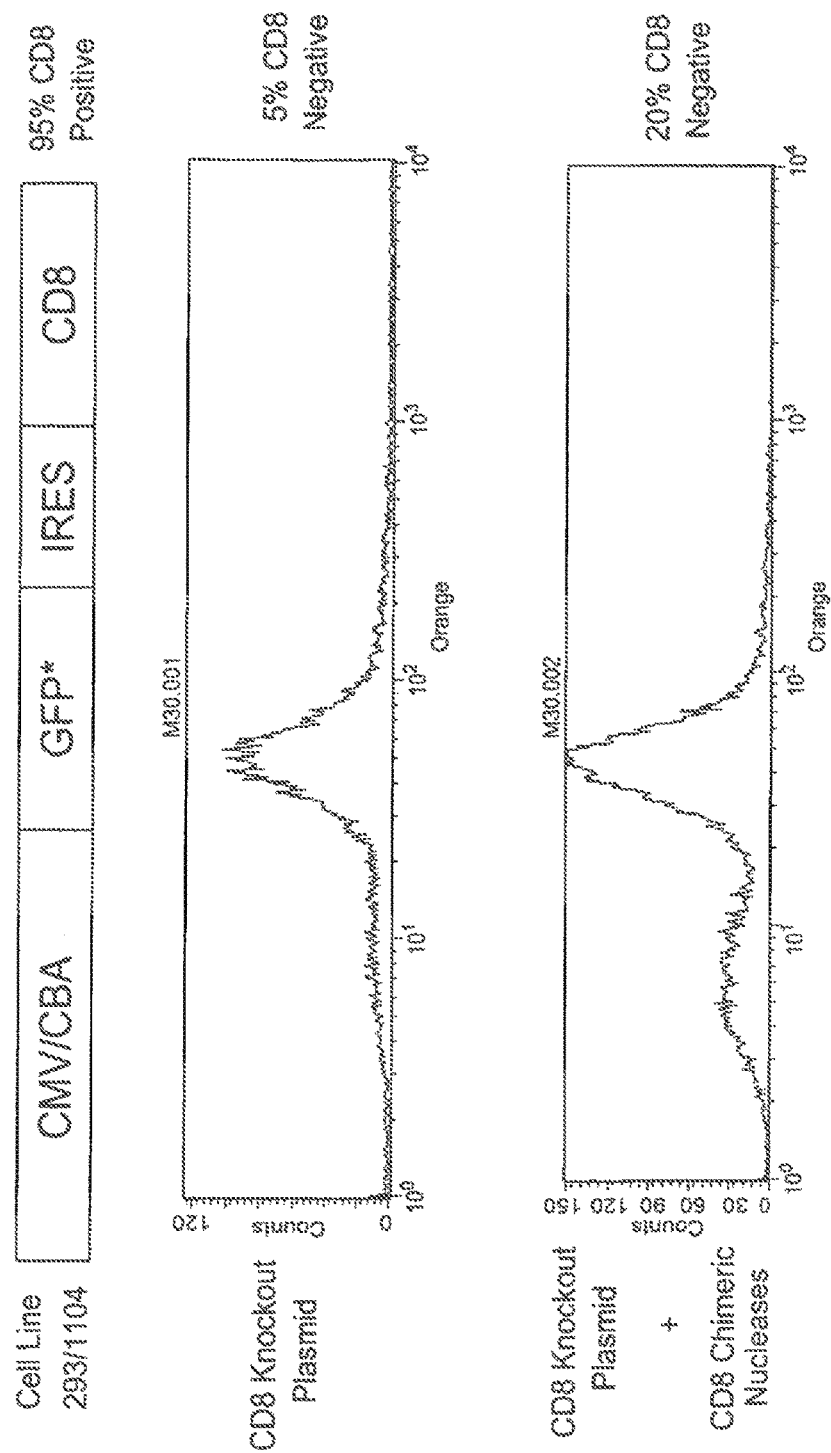

FIGS. 13A and 13B show Gene Targeting using CD8 Chimeric Nucleases. FIG. 13A shows the target sequence (SEQ ID NOs: 51 and 52) within a human CD8α gene for chimeric nucleases. FIG. 13B shows a schematic of a CMV-GFP construct (top panel) and flow cytometry plots after transfecting 293/1104 cells with the CD8 Knockout Plasmid alone (middle panel) (5% CD8 negative cells) or with the CD8 Knockout Plasmid plus the CD8 chimeric nucleases (bottom panel) (20% CD8 negative). The measurement of CD8 expression was done after selecting for puromycin resistant colonies and by staining with phycoerytherin conjugated α-CD8 monoclonal antibody.

DETAILED DESCRIPTION OF THE INVENTION

I. Overview

In certain aspects, the present invention provides methods and compositions for gene targeting with improved efficiency in a mammalian cell.

Gene targeting is a process in which the nucleotide sequence at a predetermined genomic site is selectively altered by introduction of an exogenous nucleic acid carrying a desired sequence. While not wishing to be bound to any particular mechanism, it is generally understood that the selective modification occurs by homologous recombination. Partial gene duplications, gene replacements, and gene knockouts have been created with this technology, which has the advantage that the modified gene resides at its normal chromosomal locus (Thomas et al., 1987, Cell, 51:503-512; Capecchi, 1989, Science, 244:1288-1292; Koller et al., 1992, Annu Rev Immunol, 10:705-730). In higher organisms, and in mammalian cells in particular, only very low frequencies of targeted events have been achieved, usually in the range of $10^{-6}$ per cell. In addition, gene targeting occurs against a background of non-homologous events that are 100- to 1000-fold more common (Mansour et al., 1988, Nature, 336:348-352), meaning that the exogenous nucleic acid sequence is inserted at non-selected positions on the genome.

It has been recently found that the creation of a DNA double-stranded break (DSB) in the target gene can increase the frequencies of both direct-repeat recombination and gene targeting several-thousand-fold (Brenneman et al., 1996, Proc. Natl. Acad. Sci. USA, 93:3608-3612; Choulika et al., 1995, Mol. Cell. Biol., 15:1968-1973; Donoho et al., 1998, Mol. Cell. Biol., 18:4070-4078; Rouet et al., 1994, Mol. Cell. Biol., 14:8096-8106; Sargent et al., 1997, Mol. Cell. Biol., 17:267-277; Smih et al., 1995, Nucleic Acids Res., 23:5012-5019; Taghian, et al., 1997, Mol. Cell. Biol., 17:6386-6393). As discussed in this application, Applicants have discovered that when conditions are optimized for DSB-mediated gene targeting, the frequency of gene targeting can reach 3 to 5% (see also Porteus et al., 2003, Science, 300:763). Thus, DSBs seem to be a central element of the gene targeting mechanism. Double stranded breaks (cleavages) at a site of interest can be achieved by nucleases or chemical entities which recognize and cleave the site of interest. Examples of chemical entities which recognize and cleave a site of interest are described by Dervan et al., for example, in U.S. Pat. Nos. 4,665,184, 4,942,227, 4,795,700, and 5,789,155, which references are incorporated herein in their entirety. Double stranded breaks at a site of interest can also be achieved by chimeric nucleases, as described herein.

II. Definitions

For convenience, certain terms employed in the specification, examples, and appended claims are collected here. These and other terms are defined and described throughout the application. Unless defined otherwise, all technical and scientific terms used herein have the same meaning as commonly understood by one of ordinary skill in the art to which this invention belongs.

The term "allele" is used herein to refer to any sequence that is variable between members of the same species. For example, an allele may be a single nucleotide polymorphism, a large or small deletion, a large or small insertion, a large or small inversion or a combination thereof.

As used herein, a "patient," "individual" or "subject" to be treated by the method of the invention can mean either a human or non-human animal.

The term "encodes," unless evident from its context, will be meant to include DNA sequences that encode a polypeptide, as the term is typically used, as well as DNA sequences that are transcribed into inhibitory antisense molecules.

The term "expression" with respect to a gene sequence refers to transcription of the gene and, as appropriate, translation of the resulting mRNA transcript to a protein. Thus, as will be clear from the context, expression of a protein coding sequence results from transcription and translation of the coding sequence.

The term "nuclease", as used herein, refers to any polypeptide, or complex comprising a polypeptide, that can generate double stranded breaks in genomic DNA. Examples of nucleases include restriction endonucleases, chimeric nucleases and certain topoisomerases and recombinases.

As used herein, the term "nucleic acid" refers to polynucleotides such as deoxyribonucleic acid (DNA), and, where appropriate, ribonucleic acid (RNA). The term should also be understood to include, as applicable to the embodiment being described, single-stranded (such as sense or antisense) and double-stranded polynucleotides. This term includes both naturally occurring nucleotide and artificially modified nucleotides.

"Operably linked" when describing the relationship between two DNA regions simply means that they are functionally related to each other. For example, a promoter or other transcriptional regulatory sequence is operably linked to a coding sequence if it regulates the transcription of the coding sequence.

The phrases "site of interest" and "specific site," as used herein, refer to a distinct chromosomal location at which a double stranded break (cleavage) is to be introduced, thereby inducing a cellular repair mechanism which leads to highly efficient recombinational events at that locus.

The terms "target sequence" and "target gene," as used herein, refer to a polynucleotide sequence or a gene in the chromosome selected for alteration by gene targeting. In other words, the nucleotide changes may be introduced into either a gene or a site that is not part of a genomic sequence. In certain cases, the target sequence/gene may contain a mutation that needs to be repaired or replaced. Alternatively, the target gene needs to be attenuated, inactivated, or replaced with a heterologous sequence/gene. To achieve high rate of gene targeting according to the present invention, a site of interest within workable proximity of the target sequence or within the target sequence may contain a DNA binding sequence recognizable by a chimeric nuclease so that the enzyme can make a double stranded break at or near this site.

"Transcriptional regulatory sequence" is a generic term used throughout the specification to refer to DNA sequences, such as initiation signals, enhancers, and promoters and the like which induce or control transcription of coding sequences with which they are operably linked.

As used herein, the terms "transduction" and "transfection" are art recognized and mean the introduction of a nucleic acid, e.g., an expression vector, into a recipient cell by nucleic acid-mediated gene transfer. "Transformation," as used herein, refers to a process in which a cell's genotype is changed as a result of the cellular uptake of exogenous DNA or RNA. A cell has been "stably transfected" with a nucleic acid construct when the nucleic acid construct is capable of being inherited by daughter cells. "Transient transfection" refers to cases where exogenous DNA does not integrate into the genome of a transfected cell, e.g., where episomal DNA is transcribed into mRNA and translated into protein.

III. Nucleases

In certain embodiments, the present invention provides nucleases, and particularly chimeric nucleases, which are utilized to generate a double stranded break at a site of interest within a target sequence in chromosomal DNA in a cell.

A chimeric nuclease is a chimeric protein that is designed to create a double-stranded break at one or more selected sites in the chromosome. Chimeric nucleases of the present invention comprise one or more specific DNA binding domains and one or more "cleavage" domains. The DNA binding domains confer the DNA binding specificity, while the cleavage domains confer the double-stranded break activity. A chimeric nuclease can be made as a fusion protein or by linking the DNA binding domain(s) to the cleavage domain(s).

A variety of DNA binding domains are known in the art, and any DNA binding domain that recognizes the desired site with sufficient specificity may be employed. As described herein, DNA binding domains include zinc finger binding domains.

Cleavage domains may derive from any nuclease that has DNA cleavage activity. Examples of protein types having cleavage domains include restriction enzymes, topoisomerases, recombinases, integrases and DNAses. Construction of a chimeric nuclease will generally be simplified if the cleavage domain is obtained from a nuclease that has separate domains for sequence recognition and DNA cleavage. For example, the cleavage domain may derive from a type IIs restriction endonuclease, such as the cleavage domain of the FokI restriction enzyme ("Fn"). Enzymes of this group generally have separate cleavage and sequence recognition domains. Thus, in a particular embodiment, the chimeric nucleases are fusion proteins comprising specific zinc finger binding domains and the cleavage domain of the FokI restriction enzyme (also referred to herein as the FokI cleavage domain).

The $Cys_2His_2$ zinc fingers are of particular interest in this regard. Each individual finger contacts primarily three consecutive base pairs of DNA in a modular fashion (Pavletich et al., 1991, Science, 252:809-817; Berg et al., 1996, Science, 271:1081-1085). By manipulating the number of fingers and the nature of critical amino acid residues that contact DNA directly, binding domains with novel specificities can be evolved and selected (see, e.g., Desjarlais et al., 1992, Proc. Natl. Acad. Sci. USA, 89:7345-7349; Rebar et al., 1994, Science, 263:671-673; Greisman et al., 1997, Science, 275:657-661; Segal et al., 1999, Proc. Natl. Acad. Sci. USA, 96:2758-2763). In principle, a very broad range of DNA sequences can serve as specific recognition targets for zinc finger proteins. Chimeric nucleases with several different specificities based on zinc finger recognition have already been constructed and characterized (see, e.g., Huang et al., 1996, J. Protein Chem., 15:481-489; Kim et al., 1998, Biol. Chem., 379:489-495).

The present invention contemplates chimeric nucleases that combine DNA-binding domains from natural and synthetic DNA binding proteins, such as transcription factors, with the FokI cleavage domain or other non-specific cleavage domains. For these chimeric nucleases, DNA cleavage is directed to sites recognized by the binding domains, thus permitting the manipulation of target specificity. Methods of making such chimeric nucleases are described in the art (see, e.g., Kim et al., 1994, Proc. Natl. Acad. Sci. USA, 91:883-887; Huang et al., 1996, J. Protein Chem., 15:481-489; Kim et al., 1998, Biol. Chem., 379:489-495; Nahon et al., 1998, Nucleic Acids Res., 26:1233-1239; Bibikova et al., 2001, Mol Cell Biol, 21:289-297).

In a preferred embodiment, chimeric nucleases of the present invention comprise a nuclear localization signal (NLS) which facilitates the nuclear transport of the chimeric nucleases. Essentially any NLS may be employed, whether synthetic or identified as a naturally occurring NLS, so long as the NLS is one that is compatible with the target organism. Naturally occurring mammalian nuclear localization signals are short sequences that have been identified as generally one (monopartite) or two (bipartite) clusters of four or more basic amino acids (lysine or arginine) (see, e.g., Gorlich et al., 1996, Science, 271:1513-1518; Mattaj et al., 1998, Annu Rev Biochem, 123:265-306). Other types of nuclear localization signals are known in the art, such as plant or yeast nuclear localization signals, including the yeast Mat α2-like NLS (see, e.g., Hicks et al. 1995, Plant Physiol., 107:1055-58). The SV40 large T antigen NLS is known to work in plants and mammals.

In certain embodiments, chimeric nucleases of the present invention form dimers (e.g., via binding to two cognate DNA binding sites within a target sequence), and in certain situations, dimerized chimeric nucleases stimulate gene targeting with increased efficiency. For example, chimeric nucleases can form a homodimer between two identical chimeric nucleases (e.g., via binding to two identical DNA binding sites within a target sequence). Alternatively, chimeric nucleases can form a heterodimer between two different chimeric nucleases (e.g., via binding to two different DNA binding sites within a target sequence).

In certain embodiments, the disclosure provides chimeric nucleases that are particularly effective for use in gene targeting methods. In certain gene targeting protocols, it may be desirable to cause a DNA cleavage near or at the target sequence while also keeping a limit on the number of cleavages that occur in other portions of the genome. Accordingly, it may be desirable to employ a chimeric nuclease or cooperatively acting set of chimeric nucleases that have a recognition sequence occurring rarely or uniquely in the genome to be altered. As a general principle, the larger the recognition sequence, the fewer times such sequence is likely to occur in the genome to be altered. A simple probability calculation suggests that a recognition sequence having n defined nucleotides will occur with a probability of one in $4^n$ nucleotides. According to this simplified predictive model, a recognition sequence of 11 nucleotides is most likely to occur once in the genome of an *Escherichia coli* bacterium (genome size of roughly 4.5 million bases). The human genome is estimated at a size of 3 billion base pairs, and so a chimeric nuclease having a 16 nucleotide recognition sequence is most likely to recognize only a single sequence. The simple statistical model may be adjusted to account for factors such as GC bias, repeat sequences, and heterogeneity in the target organism (e.g. humans vary by roughly 1% from each other, and such additional variation could be taken into account). Furthermore, recognition sequences may be assessed by searching for actual occurrences of the sequence in published genomic sequence of the target organism. A recognition sequence may be contiguous (an uninterrupted string of defined nucleotides, e.g., 5'-GATGTTGCT-3', SEQ ID NO: 4) or non-contiguous (interrupted by non-defined nucleotides, e.g., 5'-GATG . . . N6 . . . TTGCT-3, SEQ ID NO: 5), and in either case the frequency of occurrence can be estimated in the same way.

For gene targeting in the human genome or other organisms with a similarly sized genome, a chimeric nuclease, or two or more conjointly acting chimeric nucleases, may preferably have a recognition sequence that is at least 16 defined nucleotides in length, and optionally 17, 18, 19 or more nucleotides. As noted above, shorter sequences may be used, but may not be as effective for precise gene targeting. The term "conjointly acting" is used as a results-oriented term, meaning that the conjointly acting chimeric nucleases cause more efficient gene targeting than either nuclease alone. In certain embodiments, the invention provides a cooperatively acting pair of chimeric nucleases, each comprising a cleavage domain and a DNA binding domain, such that the conjointly acting pair recognizes a composite recognition sequence of at least 16, 17, 18, 19 or more nucleotides. Optionally, each member of the pair comprises three zinc finger domains and recognizes a sequence of 9 nucleotides. Optionally, the pair is a single chimeric nuclease that forms a homodimer. In certain embodiments, the invention provides a nucleic acid, such as a vector, comprising a sequence encoding a first chimeric nuclease and a sequence encoding a second chimeric nuclease, wherein the first and second chimeric nuclease act conjointly and recognize a composite recognition sequence of at least 16, 17, 18, 19 or more nucleotides. Optionally the first and second chimeric nucleases each comprise three zinc finger domains and recognize a sequence of 9 nucleotides. In certain embodiments, the invention provides a protein complex comprising first and second conjointly acting chimeric nucleases that recognize a composite recognition sequence of at least 16, 17, 18, 19 or more nucleotides. In view of the principles disclosed herein, it will be apparent that in organisms with smaller genomes, smaller recognition sequences may be quite effective for accurate gene targeting. Accordingly, in certain embodiments, the invention provides chimeric nucleases, or conjointly acting sets of chimeric nucleases that recognize a site of at least 6, 7, 8, 9, 10, 11, 12, 13, 14, 15 or more nucleotides. Optionally the DNA binding domains comprise one or more zinc finger domains that each confer recognition of three nucleotides. Optionally, the cleavage domain may be selected so as to be less effective when acting alone than when acting conjointly with a second cleavage domain. The use of multiple, conjointly acting chimeric nucleases may also facilitate the process of generating a nuclease or set of nucleases to mediate targeting of a particular locus.

In particular, Applicants found that in the context of human cells, a chimeric nuclease has improved efficiency when the DNA binding sites for the chimeric nucleases are oriented as inverted repeats separated by 6 nucleotides. As described in the working examples, Applicants contemplate that the nucleotide spacer between the two DNA binding sites (e.g., the two inverted repeats) may vary in length. Preferably, the nucleotide spacer may have a length of 0-20 bp (e.g., 0, 2, 4, 6, 8, 10, 15, or 20 bp). In addition, Applicants contemplate that an amino acid linker between the DNA binding domain and the cleavage domain may vary in length. Preferably, the amino acid linker may have a length of 0-30 amino acids (e.g., 0, 3, 6, 9, 12, 15, 18, 21, 24, 27, or 30 amino acids). In certain cases, in order to achieve efficient gene targeting rate, the optimal length of an amino acid linker should correlate with the length of a nucleotide spacer.

Certain aspects of the present invention relate to methods of designing a chimeric nuclease used for gene targeting. Such methods may comprise the following steps: (a) identifying a possible DNA binding sequence within workable proximity of a selected mammalian target sequence; (b) designing a DNA binding domain that binds to the DNA binding sequence identified in (a); and (c) coupling the DNA binding domain in (b) to a cleavage domain to make a chimeric nuclease. A mammalian target sequence may be selected according to the desired effect of the gene targeting. If the purpose is to develop a chimeric nuclease for use in correcting a genomic sequence that contributes to a disorder, then the target sequence will generally be the sequence to be changed. For example, any of the various alleles known to cause a genetic disorder, particularly in humans, may be selected as target sequences. If the purpose is to inactivate or attenuate a particular gene, then the target sequence may be selected such that an introduced change would, for example, introduce a stop codon early in the coding sequence, disrupt a promoter, or disrupt a start methionine codon. If the purpose is to alter the activity of a polypeptide encoded by a gene, the target site may be selected on the basis of known or predicted effects on activity of changes introduced at a particular site. If the purpose is to introduce a heterologous sequence into the genome, consideration will preferably be given to position effects on the heterologous sequence. For example, if it is a sequence to be expressed under a native promoter, then a target sequence would be selected in a region of the genome where the native promoter would effectively regulate the expression of the heterologous sequence.

Various methods for designing chimeric nucleases with varied DNA recognition sequences are known in the art. In certain embodiments, the DNA binding domain comprises one or more zinc finger domains (or referred to as zinc fingers). The zinc fingers can be engineered to recognize a selected target site in the target sequence. As described above, $Cys_2His_2$ proteins may be engineered to recognize a wide variety of sites. As another example, zinc fingers can be selected by using polypeptide display libraries. The target site is used with the polypeptide display library in an affinity selection step to select variant fingers that bind to the target site. Typically, constant zinc fingers and fingers to be randomized are made from any suitable $C_2H_2$ zinc finger protein, such as SP-1, SP-1C, TFIIIA, GLI, Tramtrack, YY1, or ZIF268 (see, e.g., Jacobs, EMBO J. 11:4507 (1992); Desjarlais & Berg, Proc. Natl. Acad. Sci. U.S.A. 90:2256-2260 (1993)). The polypeptide display library encoding variants of a zinc finger protein comprising the randomized finger, one or more variants of which will be selected, and, depending on the selection step, one or two constant fingers, is constructed according to the methods known to those in the art. Optionally, the library contains restriction sites designed for ease of removing constant fingers, and for adding in randomized fingers. Fingers are randomized, e.g., by using degenerate oligonucleotides, mutagenic cassettes, or error prone PCR. See, for example, U.S. Pat. Nos. 6,326,166, 6,410,248, and 6,479,626. Preferably, the chimeric nuclease designed in such methods further comprises a nuclear localization signal (NLS) in addition to a DNA binding domain and a cleavage domain.

The spectrum of possible recognition sequences may be compared against the region that is in workable proximity of the target sequence. To be effective for gene targeting, a DNA binding domain need that will be coupled to a cleavage domain need only bind so as to permit cleavage within a workable proximity of the target sequence. A workable proximity is any distance that still facilitates the gene targeting. In certain embodiments, a workable proximity is within at least 500 base pairs of the most distal target sequence to be changed, preferably within 200 base pairs and most preferably within 100 or 50 base pairs of the most distal target sequence to be changed. Optionally, the DNA binding domain overlaps the target sequence. Given that a target sequence is defined herein as the sequence to be altered, a target sequence may stretch over a plurality of nucleotides. In such situation, a DNA binding domain may, of course, bind within the target sequence, and the term "workable proximity" is intended to encompass this scenario. Selecting a DNA binding site may also involve evaluating the likelihood that a particular recognition sequence occurs elsewhere in the genome, and methods for doing so are described above. As described in the examples below, a variety of chimeric zinc finger nucleases may be generated. Families of such proteins will tend to bind certain consensus sequences, such as the 5' GNNGNNGNN 3' (SEQ ID NO: 6) sequence, dimers of which could recognize 5' NNCNNCNNC NNNNNN GNNGNNGNN 3' (SEQ ID NO: 7) (predicted to occur roughly once per 4096 bases in a genome). Accordingly, a region to be targeted may be scanned for a workable consensus recognition sequence, and then a zinc finger that recognizes the specific sequence may be designed. By searching a target region for a consensus sequence and then designing a suitable specified chimeric nuclease. The workability of this approach is demonstrated in example 3, and such techniques may be applied to other zinc finger nucleases and other chimeric nucleases generally.

Optionally, a method for designing a chimeric nuclease for use in gene targeting may include a process for testing the toxicity of the chimeric nuclease on a cell. Such a process may comprise expressing in the cell, or otherwise introducing into a cell, the chimeric nuclease and assessing cell growth or death rates, optionally by comparison against a control. Optionally, a method for designing a chimeric nuclease for use in gene targeting may include a process for assessing the specificity of DNA cleavage. The tendency of a chimeric nuclease to cleave at more than one position in the genome may be evaluated by in vitro cleavage assays, followed by some form of electrophoresis (e.g. pulsed field electrophoresis may be used to resolve very large fragments) and, optionally, some form of probing or Southern blotting. In view of the present disclosure, one of ordinary skill in the art may devise other tests for cleavage specificity.

Chimeric nucleases can be manufactured according to methods that are, in view of the teachings of this specification, generally known in the art. For example, the DNA binding domain(s) and cleavage domains can be produced as separate "components," which are then joined (linked) using known methods or can be produced as a single continuous unit (e.g. a fusion protein). For example, the chimeric nucleases can be manufactured by chemical synthesis or as fusion proteins by recombinant DNA/RNA technology (see, e.g., Sambrook et al., Eds., *Molecular Cloning: A Laboratory Manual,* 2nd edition, Cold Spring Harbor University Press, New York (1989); and Ausubel et al., Eds., Current Protocols in Molecular Biology, John Wiley & Sons, New York (1998). In a particular embodiment, chimeric nucleases capable of recognizing specific DNA sequences unique to a disease allele can be generated by linkage of zinc finger DNA binding domains to cleavage domains of a restriction endonuclease (e.g., the FokI cleavage domain).

In one specific embodiment, the present invention provides two chimeric nucleases, HBGZF1 and HBGZF4 (shown in FIGS. 5 and 7, respectively), for gene targeting at the beta-globin gene. In particular, HBGZF1 or HBGZF4 can form a heterodimer with another chimeric nuclease Zif-L3-Fn (also referred to herein as ZIF268), in promoting gene targeting at sequences derived from the beta-globin gene.

In another specific embodiment, the present invention provides a chimeric nuclease HCGCZF2 (shown in FIG. 10) for gene targeting at human common gamma-chain gene. In particular, HCGCZF2 can form a heterodimer with another chimeric nuclease Zif-L3-Fn, in promoting gene targeting at sequences derived from the human common gamma-chain gene.

In one embodiment, the chimeric nuclease can be directly introduced into a cell. Methods of directly introducing a polypeptide into a cell include, but are not limited to, microinjection, protein transduction, and protein therapy. For example, a protein transduction domain (PTD) can be fused to a nucleic acid encoding a chimeric nuclease, and the fusion protein is expressed and purified. Fusion proteins containing the PTD are permeable to the cell membrane, and thus cells can be directly contacted with a fusion protein (Derossi et al., 1994, Journal of Biological Chemistry, 269:10444-10450; Han et al., 2000, Molecules and Cells, 6:728-732; Hall et al., 1996, Current Biology, 6:580-587; Theodore et al., 1995, Journal of Neuroscience, 15:7158-7167). In certain cases, a chimeric nuclease may be coupled to a facilitator protein (e.g., tat, HSV VP22, and anthrax toxin). Coupling of a protein to a facilitator protein can be accomplished using methods well known to those practiced in the art.

Although some protein transduction based methods rely on fusion of a polypeptide of interest to a sequence which mediates introduction of the protein into a cell, other protein transduction methods do not require covalent linkage of a protein of interest to a transduction domain. At least two commercially available reagents exist that mediate protein transduction without covalent modification of the protein (Chariot™, produced by Active Motif; and Bioporter® Protein Delivery Reagent, produced by Gene Therapy Systems).

In another embodiment, a chimeric nuclease to be introduced into a cell is encoded by a nucleic acid, often in the form of a vector. Optionally, the chimeric nuclease is operably linked to a transcriptional regulatory element such as a promoter. In a particular embodiment, the chimeric nuclease is constructed under the control of an inducible promoter so that expression of the enzyme can be regulated in a cell. Further description of certain vectors comprising the repair substrate are described below under Section V.

There are advantages and disadvantages to each of the modes for delivering a chimeric nuclease to a cell. When a chimeric nuclease is delivered by introduction of a nucleic acid, the encoding nucleic acid needs be transcribed and translated by a cell before expression of the protein is achieved. This results in a time lag between delivery of the nucleic acid and expression of the protein. Direct delivery of a protein decreases this delay. Because proteins have a limited half-life in a cell, direct delivery of a protein often results in transient action of the protein in a cell. However, delivery with the nucleic acid permits expression of the chimeric nuclease at essentially any time after cell permeabilization, allowing greater flexibility in timing, and nucleic acids also permit transient expression of chimeric nucleases.

Other than regulating expression of a nuclease at the transcription level (e.g., by using an inducible promoter), Applicants contemplate regulating the activity of the nuclease protein. In a particular embodiment, the chimeric nuclease is fused with the hormone binding domain of the estrogen receptor so that the activity of chimeric nuclease can be regulated by administering tamoxifen (e.g., in a dose-dependent manner). Methods of making protein fusions with the hormone binding domain of the estrogen receptor are known in the art (e.g., Swenarchuk et al., 1999, Can J Microbiol, 45:480-490; Heyworth et al., 1999, Genes Dev, 13:1847-1860; Ronchini et al., 2000, Oncogene, 19:3914-3924).

In certain embodiments, a nuclease that is not a chimeric nuclease may be used to stimulate gene targeting. As disclosed herein, a native restriction endonuclease (i.e., naturally occurring, or insubstantially altered form thereof), such as SceI may be used. It is expected that the use of native restriction endonucleases in humans will, for the most part, be limited to those situations wherein the recognition site for the native endonuclease is found in a position that is sufficiently proximal to the target sequence to stimulate gene targeting. Furthermore, native restriction endonucleases with relatively small recognition sequences (e.g., native FokI, which recognizes a five base pair sequence, or EcoRI, which recognizes a six base pair sequence) are expected to generate a large number of double strand breaks in the genome of a cell, and should be used with care or in conjunction with a means of reducing the number of cleavage events. Preferred native restriction endonucleases will be those with recognition sites that are predicted to cut at about five or fewer positions in the genome of the targeted cell, and more preferably at one or two positions. Examples of such native restriction endonucleases include the members of the homing endonuclease family, including 1-SceI, I-CeuI and PI-PspI. Modifications may be made to adapt restriction endonucleases for use. For example, the portion of a restriction endonuclease that mediates DNA binding may be modified so as to alter the recognition site. Preferably such modification may create an altered nuclease that recognizes a site within useful proximity of a target sequence. Enzymes with separate cleavage and recognition domains, such as FokI and other type IIs restriction enzymes, may be particularly amenable to such modification. Instead of, or in combination with, a modification of the restriction enzyme, a sequence proximal to the target sequence may also be altered to introduce a recognition site for a native restriction endonuclease. This may be achieved by an initial gene targeting step using, for example, a chimeric nuclease. Any of the nucleases disclosed herein may be fused to a nuclear localization signal that is suitable for the subject cell type.

IV. Repair Substrates

In certain aspects, the present invention relates to repair substrates for gene targeting. The term "repair substrate," as used herein, generally refers to a nucleic acid introduced in a cell for altering a target sequence in chromosomal DNA. The term "repair substrate" is used for convenience, and, as indicated throughout the specification, a repair substrate is not limited to the purpose of repairing a target sequence. A repair substrate can be used for other purposes such as modifying, replacing, attenuating or inactivating a target sequence. A repair substrate may also be used to insert a large stretch of new sequence at a particular position. For example, in a process termed "transgenesis" a desired gene sequence may be inserted at a position that is expected to provide expression of the gene at therapeutically effective levels. A repair substrate includes: (i) a polynucleotide sequence that is substantially identical to a region proximal to or flanking a target sequence; and (ii) a polynucleotide sequence which replaces the target sequence upon recombination between the repair substrate and the target sequence.

A repair substrate is designed such that it contains a polynucleotide sequence which is substantially identical to the target gene (target sequence). In certain cases, the polynucleotide sequence is at least several hundred base pairs long and has portions on either side of the target sequence which can be designated as the left and right arms of the repair substrate.

As described herein, the phrase "substantially identical" means that this polynucleotide sequence is sufficient to mediate homologous recombination between the repair substrate and the target gene in chromosome. For example, this polynucleotide sequence may be at least 90%, 95%, 97%, 98%, 99% or 100% identical to the corresponding target sequence. It is preferred that the sequence variations in this polynucleotide sequence do not cause amino acid changes (e.g. wobble mutations) or only cause conservative amino acid replacements. Conservative replacements are those that take place within a family of amino acids that are related in their side chains (see, for example, Biochemistry, 2nd ed., Ed. by L. Stryer, W.H. Freeman and Co., 1981). For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule.

In certain embodiments, the corresponding homologous nucleotide sequences in the target sequence flank a specific site for cleavage and/or a specific site for introducing the desired sequence changes. The distance between the specific cleavage site and the homologous nucleotide sequences (e.g., each arm) can be several hundred nucleotides. Preferably, the distance between them is below 200 nucleotides (e.g., 0, 10, 20, 30, 50, 75, 100, 125, 150, 175, and 200 nucleotides). In most cases, a smaller distance may give rise to a higher gene targeting rate. In a preferred embodiment, the repair substrate is substantially identical, across its entire length except for the sequence changes to be introduced, to a portion of the genome that encompasses both the specific cleavage site and the portions of sequence to be altered.

A repair substrate also contains a polynucleotide sequence that is being introduced into the genome. Specifically, this polynucleotide sequence can be used to repair, modify, replace, attenuate or inactivate a target gene upon homologous recombination between the repair substrate and the target gene. Optionally, the sequence changes can contain a heterologous sequence (e.g., a mutation) to be introduced in a target gene. Typically, this polynucleotide sequence is flanked by each end of the polynucleotide sequence used to mediate homologous recombination.

In a particular embodiment, a repair substrate is designed to contain wobble mutations in its DNA binding site (i.e. mutations in the third position of a codon that do not change the amino acid encoded) for a chimeric nuclease so that after gene targeting occurs, the chimeric nuclease cannot bind to the new target gene.

In certain embodiments, a repair substrate to be introduced into a cell can be inserted in a vector. Optionally, the repair substrate is operably linked to a transcriptional regulatory sequence such as a promoter. Details of the vector encoding a repair substrate are described below under Section V.

In a preferred embodiment, the repair substrate and the chimeric nuclease can be introduced into the cell on a single vector. A single vector configuration may increase the efficiency for gene targeting.

V. Vectors

As described above, repair substrates and nucleases to be introduced into a cell can be inserted in a vector, and optionally a repair substrate and chimeric nucleases may be encoded on a single plasmid. As used herein, a "vector" includes a nucleic acid vector, for example, a DNA vector (e.g., a plasmid), a RNA vector, virus or other suitable replicon (e.g., viral vector). Vectors of the present invention may be in the supercoiled form or in the linearized form.

In embodiments where the chimeric nuclease is to be provided as a protein, a recombinant chimeric nuclease can be produced by ligating the cloned gene, or a portion thereof, into a vector suitable for expression in either prokaryotic cells, eukaryotic cells (yeast, avian, insect or mammalian), or both. Expression vehicles for production of a recombinant chimeric nuclease include plasmids and other vectors. For instance, suitable vectors for the expression of a chimeric nuclease include plasmids of the types: pBR322-derived plasmids, pEMBL-derived plasmids, pEX-derived plasmids, pBTac-derived plasmids and pUC-derived plasmids for expression in prokaryotic cells, such as E. coli.

Mammalian expression vectors may contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17.

Various viral vectors which can be utilized for introducing chimeric nucleases and/or repair substrates into cells. These viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicularstomatitis virus), paramyxovirus (e.g. measles and Sendai), positive strand RNA viruses such as picornavirus and alphavirus, and double stranded DNA viruses including adenovirus, herpes virus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example.

For example, a retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) may be utilized.

Vectors may transfer or incorporate a gene for a selectable marker so that transduced cells can be identified and generated. In certain embodiments a selectable marker is a counter selectable marker that facilitates the elimination of cells carrying the marker. By inserting a sequence of interest into the viral vector, along with another gene which encodes the ligand for a receptor on a specific target cell, for example, the vector is target-specific. Viral vectors can be made target-specific by attaching, for example, a sugar, a glycolipid or a protein. Those skilled in the art will know of, or can readily ascertain without undue experimentation, specific polynucleotide sequences which can be inserted into the viral genome or attached to a viral envelope to allow target-specific delivery of a viral vector. Examples of viral vectors are known in the art (e.g., Coffin, J. M., Retroviridae: The viruses and their replication, In Fundamental Virology, Third Edition, B. N. Fields, et al., Eds., Lippincott-Raven Publishers, Philadelphia, 1996), and described, for example, in McVey et al., U.S. Pat. No. 5,801,030, the teachings of which are incorporated herein by reference.

A vector comprising a nucleic acid encoding a chimeric nuclease contains all or part of the coding sequence for the chimeric nuclease operably linked to one or more transcriptional regulatory sequences whereby the coding sequence is under the control of transcription signals to permit production or synthesis of the chimeric nuclease. Such transcriptional regulatory sequences include promoter sequences, enhancers, and transcription binding sites. Exemplary constitutive promoters include, but are not limited to, cytomegalovirus promoter (CMV), SV40 early promoter, Rous Sarcoma Virus (RSV) promoter, phosphoglycerate kinase promoter (PGK), and chicken beta-actin promoter (CBA). For added control, the chimeric nuclease may be under the control of an inducible promoter. Exemplary inducible promoters include, but are not limited to, $Zn^{2+}$ metallothionein promoter, metallothionein-1 promoter, human metallothionein IIA promoter, lac promoter, laco promoter, mouse mammary tumor virus early promoter, mouse mammary tumor virus LTR promoter, triose dehydrogenase promoter, herpes simplex virus thymidine kinase promoter, simian virus 40 early promoter, and retroviral myeloproliferative sarcoma virus promoter. Another inducible system that can be useful is the Tet-Off™ or Tet-On™ system (Clontech, Palo Alto, Calif.) originally developed by Gossen and Bujard (Gossen and Bujard, 1992, Proc. Natl. Acad. Sci. USA, 89:5547-5551; Gossen et al., 1995, Science, 268: 1766-9). This system also allows high levels of gene expression to be regulated in response to tetracycline or tetracycline derivatives such as doxycycline. Selection of the promoters will generally depend upon the desired route for expressing the chimeric nuclease.

Vectors comprising nucleic acids encoding other types of nucleases may also be chosen and designed as described above. In certain embodiments, the application provides a vector comprising a repair substrate and a nucleic acid encoding a nuclease. As described herein, the nuclease is optionally a chimeric nuclease, but may also be another type of nuclease. A vector may comprise sequences encoding two or more nucleases, and particularly chimeric nucleases. A preferred vector encodes two chimeric nucleases that act conjointly to facilitate gene targeting.

Methods of constructing the vectors containing nucleases and/or repair substrates are well known in the art (see, e.g., Sambrook et al., Eds., *Molecular Cloning: A Laboratory Manual,* 2nd edition, Cold Spring Harbor University Press, New York (1989); and Ausubel et al., Eds., Current Protocols In Molecular Biology, John Wiley & Sons, New York (1997)). For example, the nucleic acid elements can be isolated from nature, modified from native sequences or manufactured de novo (e.g., by chemical synthesis or recombinant DNA/RNA technology). These elements can then be isolated and ligated together by methods known in the art, such as exploiting and manufacturing compatible cloning or restriction sites.

Vectors comprising chimeric nucleases and/or repair substrates can be introduced into a cell by a variety of methods (e.g., transformation, transfection, direct uptake, projectile bombardment, using liposomes). Examples of suitable methods of transfecting or transforming cells include calcium phosphate precipitation, electroporation, microinjection, infection, lipofection and direct uptake. Such methods are described in more detail, for example, in Sambrook et al., *Molecular Cloning: A Laboratory Manual,* 2nd Edition, Cold Spring Harbor University Press, New York (1989); and Ausubel, et al., Current Protocols in Molecular Biology, John Wiley & Sons, New York (1998), the teachings of which are incorporated herein by reference. In certain cases, a vector comprising chimeric nucleases and/or repair substrates can also be introduced into a cell by targeting the vector to cell membrane phospholipids. For example, targeting of a vector of the present invention can be accomplished by linking the vector molecule to a VSV-G protein (a viral protein with affinity for all cell membrane phospholipids). Such a construct can be produced using methods well known to those practiced in the art.

VI. Cells

As used herein, a cell refers to a prokaryotic cell (e.g., a bacterial cell), or a eukaryotic cell (e.g., an animal, plant or yeast cell). A cell which is of animal or plant origin can be a stem cell or somatic cell. Suitable animal cells can be of, for example, mammalian, avian or invertebrate origin. Examples of mammalian cells include human, bovine, ovine, porcine, murine (such as murine embryonic stem cells), rabbit and monkey cells. The cell may be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions). A preferred cell is a human cell. In the case of a plant cell, whole plants may be regenerated from genetically altered cells by, for example, callus regeneration techniques.

The cells as used herein, include cultured cells and cell lines. The cell can be an in vitro cell (e.g., outside an animal's body), or an in vive cell (e.g., inside an animal's body). The cell can be obtained commercially or from a depository or obtained directly from an individual, such as by biopsy. The cells can be obtained from an individual in need, to whom the cells will be reintroduced once the cells are modified in vitro. Alternatively, the cells can be obtained from another different individual (donor) of the same or different species. For example, nonhuman cells, such as pig cells, can be modified in vitro to include a DNA construct and then introduced into a human. In other cases, the cells need not be isolated from an individual where, for example, it is desirable to deliver the vector to cells of the individual for in vivo gene therapy.

In certain embodiments, the application provides a cell comprising a chimeric nuclease and a repair substrate. In certain embodiments, the application provides a cell comprising a nucleic acid encoding a chimeric nuclease and a repair substrate. Preferably the cell is a mammalian cell, most preferably a human cell. The cell need not be stably designed to comprise a chimeric nuclease and a repair substrate; instead the cell may comprise the chimeric nuclease and/or the repair substrate for a brief period of time. As disclosed herein, prolonged expression of a nuclease may compromise the viability of a cell, and therefore it may be preferable that the nuclease be present or active in the cell for only so long as is needed to effect gene targeting. The transient presence of a chimeric nuclease in a cell may be achieved, for example, by direct introduction of the protein, by transient transfection with a non-integrating vector encoding the chimeric nuclease, by transient or non-transient transfection with a nucleic acid expressing a chimeric nuclease under control of an inducible or otherwise controlled promoter. Transient activity of a nuclease in a cell may be achieved, as described above, by coupling the nuclease to a polypeptide such as tamoxifen responsive portion of an estrogen receptor.

VII. Methods for Gene Targeting

Certain aspects of the present invention relate to methods of changing a target sequence in chromosomal DNA through gene targeting in a mammalian cell. In one specific embodiment, the method can be used to modify a target sequence. In another specific embodiment, the method can be used to repair a target sequence. In another specific embodiment, the method can be used to attenuate or inactivate a target sequence/gene. In a further specific embodiment, the method can be used to introduce a heterologous sequence into a site of interest in the chromosome.

Such methods may comprise the following steps: (a) introducing a chimeric nuclease into the cell, wherein said chimeric nuclease comprises: (i) a DNA binding domain; and (ii) a cleavage domain; and (b) introducing a repair substrate into the cell, wherein said repair substrate comprises: (i) a polynucleotide sequence that is substantially identical to a region on one or both sides of the target sequence; and (ii) a polynucleotide sequence which changes the target sequence upon recombination between the repair substrate and the target sequence. Upon recombination between the repair substrate and the target sequence, the target sequence is changed so as to match the repair substrate. Optionally, in such methods for gene targeting, the chimeric nuclease and the repair substrate are introduced into a cell on a single vector. Preferably, the chimeric nuclease used in such methods further comprises a nuclear localization signal (NLS) in addition to a DNA binding domain and a cleavage domain.

In certain embodiments, the repair substrate and/or the chimeric nuclease are operably linked to a promoter in a vector. Optionally, the promoter is an inducible promoter. Details of the vectors and methods of introducing the chimeric nuclease and/or repair substrate into a cell are described above.

Gene targeting methods may be used to introduce a transgene for expression in the cell ("transgenesis"). For example, a genetic disease caused by a decrease in the level of a necessary gene product may be treated or ameliorated by providing a transgene expressing the needed gene product. The transgene may be targeted to the location of the endogenous gene, or to a different location. In a particular embodiment of the subject method, the site of interest is a transcriptionally active location, or an "open location" in chromosome. The term "open location," as used herein, refers to a specific chromosomal location that is known to support transcription. There is considerable evidence to suggest that a heterologous gene inserted at an open location will be expressed more effectively than a heterologous gene inserted elsewhere.

In a particular embodiment, the present invention contemplates inducing gene targeting in the presence of an inhibitor of the non-homologous end joining (NHEJ) pathway. On one hand, such inhibitors can increase the rate of gene targeting. On the other hand, such inhibitors can decrease the rate of the unwanted non-homologous recombination events. It is known that in order to maintain genomic integrity, higher eukaryotes have evolved multiple pathways for the repair of double stranded breaks (DSB) in a cell, including non-homologous end joining (NHEJ). NHEJ joins together double stranded DNA ends after they are modified, and is regarded as the dominant mechanism for DSB repair in vertebrates, especially in Go and GI phases of the cell cycle (Khanna et al., 2001, Nat. Genet., 27:247-254).

Examples of inhibitors of the NHEJ pathway include any compound (agent) that inhibits or blocks either expression or activity of any protein component in the NHEJ pathway. Protein components of the NHEJ pathway include, but are not limited to, Ku70, Ku86, DNA protein kinase (DNA-PK), Rad50, MRE11, NBS1, DNA ligase IV, and XRCC4. An exemplary inhibitor is wortmannin which inhibits at least one protein component (e.g., DNA-PK) of the NHEJ pathway.

Another example of such inhibitors can be an RNAi construct that blocks expression of a protein component of the NHEJ pathway (e.g., DNA-PK or DNA ligase IV). As used herein, the term "RNAi construct" is a generic term including small interfering RNAs (siRNAs), hairpin RNAs, and other RNA or RNA:DNA species which can be cleaved or dissociated in vive to form siRNAs. It is known that RNAi (RNA interference) provides a useful method of inhibiting gene expression in vitro or in vivo. RNAi constructs may comprise long stretches of dsRNA identical or substantially identical to the target nucleic acid sequence or short stretches of dsRNA identical to substantially identical to only a region of the target nucleic acid sequence, although in mammalian cells, a shorter RNAi construct is preferred so as to avoid triggering any cellular immune responses. For example, RNAi constructs having a length of 18 to 30 nucleotides may be employed, and preferably RNAi constructs having a length of 18 to 25 nucleotides. RNAi constructs herein also include expression vectors capable of giving rise to transcripts which form dsRNAs or hairpin RNAs in cells, and/or transcripts which can produce siRNAs in vivo. Methods of making and using RNAi constructs are described in published U.S. Patent Publication Nos. US20020086356, US20020162126, US20030084471, and US20030108923. RNAi constructs may be administered as naked nucleic acids or in a complex with various cationic moieties or lipids.

Methodologies to decrease non-homologous recombination are particularly relevant in view of recent results in the gene therapy treatment of patients suffering from Severe Combined Immunodeficiency. In these gene therapy trials, the curative gene was introduced by non-homologous recombination. In rare instances, the gene incorporated in such a way as to activate an oncogene, and although recipients showed initial benefit, many now suffer from leukemia. As described above, NHEJ inhibitors may decrease the incidence of non-homologous integration. In an ex vivo setting, it is also possible to eliminate or select against cells in which a non-homologous recombination event has occurred. For example, any introduced nucleic acid, such as a nucleic acid encoding a chimeric nuclease, a repair substrate, or part or all of a vector, may be incorporated non-homologously into the genome of the cell that is the subject of gene targeting. Cells containing non-homologously recombined material may be eliminated by a variety of methods. For example, a nucleic acid introduced into the cell may be designed to include a counter selectable marker, such as a viral thymidylate kinase gene (e.g. HSV-tk), that causes the elimination of any cell containing such marker. Thus, if only homologous recombination occurs, only the repair substrate sequence should be inserted into the genome. If non-homologous recombination occurs, an entire construct containing the counter-selectable marker is likely to be incorporated into the genome. Cells containing such markers may be eliminated by the counterselection treatment, which, in the case of the HSV-tk gene, is typically treatment with the antiviral agent gancyclovir. A marker may also be one that permits rapid sorting, such as a fluorescent protein marker (e.g., Green Fluorescent Proteins and the like), through a process such as Fluorescence Activated Cell Sorting (FACS).

In certain aspects, the present invention provides methods of ameliorating, treating or preventing diseases in an individual by gene targeting. For example, an allele may contribute to a disease by increasing the individual's susceptibility to the disease or by being a direct causal contributor to the disease. Accordingly, by changing the sequence of the allele, the disease may be ameliorated, treated or prevented. The individual may be a mammal or other animal. A preferred individual is a human.

More than 3,000 diseases are caused by mutations, including sickle cell anemia, hemophilia, severe combined immunodeficiency (SCID), Tay-Sachs disease, Duchenne's muscular dystrophy, Huntington's disease, alpha-thalassemia, and Lesch Nyhan syndrome. Accordingly, all these genetic diseases are within the scope of the present invention.

Specifically, certain embodiments of the present invention are particularly suitable for diseases where corrected cells by gene targeting have a significant selective advantage over mutant cells. An example of such diseases is severe combined immunodeficiency (SCID) which is mainly caused by mutation in the human common gamma-chain. The gene targeting rates of 3-5% (as demonstrated by the present invention) would likely be curative for these types of diseases.

Certain embodiments of the present invention are also suitable for diseases where cells corrected by gene targeting have no significant selective advantage over mutant cells. Two examples of such diseases are sickle cell disease which is caused by a single nucleotide substitution in the beta-globin gene, and hemophilia which mainly results from mutations in factor VIII or factor IX. The gene targeting rates of 3-5% (as demonstrated by the present invention) are expected to be sufficient to ameliorate or even cure the diseases since a small percentage of corrected cells may have a dramatic benefit.

In certain embodiments, the subject methods may be used to alter a genomic target sequence that renders a subject susceptible to an infectious disease. For example, many viral and bacterial pathogens enter a cell by binding to and recruiting a set of cell surface and intracellular proteins. Gene targeting may be used to eliminate or attenuate such a binding site or entry mechanism. An exemplary target gene is the CCR5 gene that participates in HIV entry into T cells. Cells of an individual who is infected with HIV or susceptible to HIV infection may be treated so as to decrease the ability of HIV to enter the cells. For example, the cell may be a T cell or a T cell progenitor such as a hematopoietic stem cell.

Certain methods described herein may be applied to cells in vitro or applied to subjects, thereby effecting gene targeting in vivo.

Chimeric nucleases and vectors of the present invention can be introduced into an individual using routes of administration generally known in the art (e.g., parenteral, mucosal, nasal, injection, systemic, implant, intraperitoneal, oral, intradermal, transdermal, intramuscular, intravenous including infusion and/or bolus injection, subcutaneous, topical, epidural, buccal, rectal, vaginal, etc.).

In certain aspects, chimeric nucleases and vectors of the present invention can be formulated in combination with a suitable pharmaceutically acceptable carrier (excipient), such as saline, sterile water, dextrose, glycerol, ethanol, Ringer's solution, isotonic sodium chloride solution, and combinations thereof. Formulation should suit the mode of administration, and is well within the skill of the art. The mode of administration is preferably at the location of the target cells.

Chimeric nucleases and vectors of the present invention may be administrated to an individual, alone or in conjunction with other therapeutic agents. These different types of therapeutic agents may be administered in the same formulation or in a separate formulation.

The dosage of chimeric nucleases or vectors of the present invention administered to an individual, including frequency of administration, will vary depending upon a variety of factors, including mode and route of administration; size, age, sex, health, body weight and diet of the recipient; nature and extent of symptoms of the disease or disorder being treated; kind of concurrent treatment, frequency of treatment, and the effect desired; the nature of the formulation; and the judgment of the attending practitioner. Variations in these dosage levels can be adjusted using standard empirical routines for optimization, as is well understood in the art.

The present invention is illustrated by the following examples, which are not intended to be limiting in any way.

EXAMPLES

Example 1

Chimeric Nucleases Stimulate Gene Targeting in Mammalian Cells

Gene targeting is a powerful technique for introducing genetic change into the genome of eukaryotic cells. To augment the power of this technique, Applicants have systematically investigated the variables that regulate gene targeting. It is evident that local double-stranded DNA breaks are a powerful stimulus for gene targeting. Thus, Applicants have adapted chimeric nucleases, protein fusions that can be designed to recognize a wide variety of DNA sequences, to stimulate gene targeting up to therapeutically and experimentally useful levels in human somatic cells. This appears to be the first gene targeting in a manner using a chimeric nuclease.

Since the discovery that sickle cell anemia is caused by a single base pair mutation, it has been a goal to cure the disease by correcting the mutation. With the understanding that numerous diseases are caused by similar small mutations in single genes, the importance of being able to cure disease by gene correction has only increased. Conceptually, one method of gene correction is to adopt the strategy of gene targeting that is used to create genetic change in murine embryonic stem (ES) cells and use it in human somatic cells (Capecchi, 1989, Science, 244:1288-1292; Doetschman et al., 1987, Nature, 330:576-8). Such a strategy has been precluded by the extremely low spontaneous rate of gene targeting when DNA is introduced into human somatic cells (Sedivy et al., 1989, Proc. Natl. Acad. Sci. USA, 86:227-231). It is known, however, that the creation of a DNA double-stranded break (DSB) in the genomic target can stimulate the process by over a thousand fold (DSB-induced gene targeting or DSB-GT) (Choulika et al., 1995, Molecular and Cellular Biology, 15:1968-1973; Smih et al., 1995, Nucleic Acids Res, 23:5012-9; Donoho et al., 1998, Mol Cell Biol, 18:4070-8; Sargent et al., 1997, Mol Cell Biol, 17:267-77; Brenneman et al., 1996, Proc Natl Acad Sci USA, 93:3608-12). Applicants describe herein a system to systematically explore the factors that regulate DSB-induced gene targeting. Applicants used this system to demonstrate that chimeric nucleases can be potent stimulators of gene targeting in the genome of human somatic cells.

The system Applicants used to study gene targeting is depicted in FIG. 1 and was based on the correction of a mutated green fluorescent protein (GFP) gene ("GFP gene targeting system"). A single copy of an artificial gene target (A658) was stably integrated into the genome of 293 cells, and found that the maximum number of GFP positive cells occurred 2.5-3 days after transfection and remained stable for at least two weeks (FIG. 1D). The gene targeting reaction, therefore, occurred relatively quickly after transfection and created stable genetic change. Finally, Applicants purified single GFP positive cells by fluorescence activated cell sorting and determined the sequence of the GFP gene after gene targeting. In the 9 GFP positive cells tested, the sequence of the GFP gene was wild-type, demonstrating that gene targeting had occurred (data not shown). The DSB-GT rate in murine 3T3 and human SaOS-2 cells was similar to that in 293 cells (data not shown). Further, the DSB-GT rate was similar whether a pool of cells (FIG. 3B) or a clonal cell line (FIG. 1C) with single insertion sites for A658 was examined. Thus, our findings were not cell type or integration site dependent.

Applicants then explored the variables that regulate the rate of DSB-GT. Applicants found that increasing the amount of substrate (RS2100) transfected increased the rate of DSB-GT until a plateau is reached (FIG. 2A). This result demonstrated that gene targeting is dependent on the amount of repair substrate available. Applicants found that increasing the length of homology between the repair substrate and the target linearly increased the rate of DSB-GT (FIG. 2B). In these experiments, Applicants kept the amount of 5' homology constant at 290 basepairs (bp) and varied the amount of 3' homology from 500 bp to 3700 bp. This result suggests that while spontaneous gene targeting is logarithmically dependent on homology length (Deng et al., 1992, Molecular and Cellular Biology, 12:3365-3371), DSB-GT is linearly dependent on homology length. In either case, increasing the length of homology between the damaged target and the repair substrate increased the frequency with which the cell undergoes gene targeting. FIG. 2C shows that the DSB-GT rate was linearly dependent on the amount of PGK-Sce transfected. The DSB-GT rate plateaued, however, when higher amounts of CBA-Sce were transfected (FIG. 2C). This data suggests that DSB-GT is dependent on the creation of a DSB to initiate gene targeting but eventually becomes saturated for DSB creation. Applicants found that manipulating the transcriptional status of the repair substrate can affect the rate of gene targeting. Transcribing the truncated repair substrate with a CMV promoter (CMV-RS2100) increased the rate of DSB-GT by 50% (FIG. 2D). Just as with RS2100, transfecting CMV-RS2100 into 293-0 cells did not generate GFP positive cells (data not shown). The rate of DSB-GT was highest when Sce expression is driven by the CBA promoter, intermediate with the PGK promoter, and lowest with the CMV promoter (FIG. 2E). This result probably reflects the different levels of Sce expression from each promoter. FIG. 2E also demonstrates that the rate of DSB-GT can be increased by placing the repair substrate on the same plasmid as the Sce expression cassette rather than co-transfecting two plasmids. The stimulation was lost when the DSB-GT process was at saturation as when the CBA promoter was used to express Se. When Applicants optimized the above parameters Applicants achieved gene targeting rates of 3-5% (FIG. 2E, CBA promoter).

In the GFP gene targeting system the introduction of a DSB stimulated GT by >2000-fold and the absolute rate of gene targeting reached 3-5% when conditions were optimized. Such a system, however, depended on the prior introduction of a Sce site into the target gene and therefore can not be used for endogenous genes. To stimulate gene targeting at endogenous genes, a method to create sequence specific DSBs in those genes needs to be developed. Chimeric nucleases have such potential (Chandrasegaran et al., 1999, Biol Chem, 380:841-8). Chimeric nucleases-fusions between zinc finger binding DNA binding domains and the endonuclease domain of the FokI restriction enzyme ("Fn")—can site-specifically cleave naked DNA in vitro (Chandrasegaran et al., 1999, Biol Chem, 380:841-8), extrachromosomal DNA in *Xenopus* oocytes (Bibikova et al., 2001, Mol Cell Biol, 21:289-97) and chromosomal DNA in *Drosophila* (Bibikova et al., 2002, Genetics, 161:1169-75). Applicants decided to try to extend this methodology to stimulate gene targeting in human somatic cells (FIG. 3). FIG. 3A shows the structure of the expression plasmids and target sites for the chimeric nuclease experiments. Applicants designed three different chimeric nucleases, each driven by the CMV promoter and containing a nuclear localization signal at their amino-termini (FIG. 3A). In two constructs (CMV-QQR-L18-Fn and CMV-QQR-L0-Fn) the DNA binding specificity was conferred by the artificial QQR three zinc finger domain that binds with nanomolar affinity to the sequence 5' GGGGAAGAA 3' (SEQ ID NO: 8) (Shi et al., 1995, Science, 268:282-284). These two constructs differed in the length of the amino acid linker between the zinc fingers and the Fn domain. The amino acid linker was 18 amino acids in CMV-QQR-L18-Fn while in CMV-QQR-L0-Fn there was no amino acid linker. CMV-ZIF-L3-Fn fused the three zinc fingers from Zif268 to the Fn domain with a 3 amino acid linker between the two domains. The Zif268 zinc finger domain recognizes the sequence 5' GCGTGGGCG 3' (SEQ ID NO: 9) with sub-nanomolar affinity (Elrod-Erickson et al., 1999, J Biol Chem, 274: 19281-5). Applicants constructed three cell lines (293/QQR8, 293/QQR6, 293/QQRZIF6) with corresponding gene targets (QQR8, QQR6, and QQRZIF6). QQR8 and QQR6 have inverted repeats of the QQR binding site inserted next to the Sce recognition site (FIG. 3A). QQR8 and QQR6 differed in that the repeats are separated by 8 bp in QQR8 and 6 bp in QQR6. Prior work has shown that purified QQR-Fn protein without an amino acid linker (equivalent to CMV-QQR-L0-Fn) cuts DNA most efficiently when the inverted DNA binding sites are separated by 6 bp while purified QQR-Fn protein with an 18 amino acid linker (equivalent to CMV-QQR-L18-Fn) cuts DNA when the binding sites are separated by either 6 or 8 bp (Bibikova et al., 2002, Genetics, 161:1169-75; Smith et al., 2000, Nucleic Acids Res, 28:3361-9). In all of the chimeric nuclease gene targeting experiments, Applicants co-transfected the chimeric nuclease with the repair substrate RS2700 (FIG. 1A).

Applicants found that the QQR chimeric nucleases stimulated DSB-GT (FIG. 3B). While the background rate of spontaneous gene targeting in 293 cells was 0.71 events per million transfected cells (FIG. 1C), the CMV-QQR-L18-Fn chimeric nuclease stimulated gene targeting 17-fold on target QQR6 and 260-fold on target QQR8 (FIG. 3B). More strikingly, CMV-QQR-L0-Fn did not stimulate gene targeting on target QQR8 but stimulated gene targeting by over 2000-fold on target QQR6 (FIG. 3B). Thus, CMV-QQR-L18-Fn showed some preference for QQR8 over QQR6 while CMV-QQR-L0-Fn showed a dramatic preference for QQR6 over QQR8. These results demonstrate, therefore, that removing the amino acid linker between the zinc finger and the nuclease domains increased both the activity and specificity of the fusion protein. Moreover, CMV-QQR-L0-Fn was as efficient as Sce in stimulating gene targeting on target QQR6. If the chimeric nucleases did not have a nuclear localization signal they were unable to stimulate gene targeting (data not shown). They were also unable to stimulate gene targeting if there was a single zinc finger binding site rather than an inverted repeat binding site (data not shown). CMV-ZIF-L3-Fn was not able to stimulate gene targeting in either 293/QQR8 or 293/QQR6 cell lines showing that stimulation depended on having the cognate DNA binding site in the target gene (data not shown). Overall, these results demonstrate that homodimers of chimeric nucleases were extremely potent stimulators of gene targeting in the genome of human somatic cells.

To explore further the specificity and efficiency of DSB-GT induced by chimeric nucleases, Applicants tested whether heterodimers of chimeric nucleases could stimulate gene targeting. In cell line 293/QQRZIF6 the target GFP gene was disrupted by inverted binding sites for the QQR and Zif268 zinc fingers separated by 6 bp. Transfection of either CMV-QQR-L0-Fn or CMV-ZIF-L3-Fn alone did not result in significant stimulation of gene targeting (FIG. 3C). When Applicants co-transfected both chimeric nucleases, however, Applicants were able to stimulate gene targeting by over 5000-fold and the stimulation was as efficient as Sce (FIG. 3C). Heterodimers of chimeric nucleases, therefore, can cleave genomic target sequences to stimulate gene targeting several thousand fold.

Applicants found one important difference between Sce and the chimeric nucleases in stimulating gene targeting. When Applicants used Sce to stimulate gene targeting, the number of GFP positive cells reached a maximum at 3 days and then remained stable (FIG. 1D). When Applicants used the chimeric nucleases to stimulate gene targeting, however, Applicants found that the number of GFP positive cells decreased with time after day 3 (FIG. 3D). The decrease in GFP positive cells suggests that continuous expression of these nucleases, including one that has a very specific binding site (Zif268), is toxic to cells.

The ability to correct mutations by gene targeting is a conceptually elegant form of gene therapy that has been precluded by its low rate in human somatic cells. Applicants have found that DSB-GT is a process that is dependent on the length of homology between genomic target and repair substrate, the amount of repair substrate in the cell, the frequency of DSBs at the target, and the transcriptional status of the repair substrate. When Applicants optimize these parameters, Applicants achieve gene targeting rates of 3-5%. Such rates of gene targeting are of a therapeutically and experimentally useful magnitude. In diseases where corrected cells have a powerful selective advantage over mutant cells, such as severe combined immunodeficiency (SCID), gene correction rates of 3-5% would almost certainly be curative. In other diseases, such as sickle cell disease, in which selective advantage for corrected cells is only imposed in post-replicative cells, a correction rate of 3-5% may only ameliorate the disease. Finally, in diseases in which there is no selective advantage for corrected cells but where small numbers of corrected cells may have a dramatic benefit, such as hemophilia, targeting rates of 3-5% may be sufficient to ameliorate or even cure.

Applicants used the GFP system to show that chimeric nucleases can stimulate gene targeting in human somatic cells by at least several-thousand fold. This result has powerful implications. Chimeric nucleases are modular in nature with the DNA binding specificity residing in the zinc finger domain. By modifying the DNA binding specificity of the zinc finger domain, they can be engineered and optimized to bind specifically to a wide variety of nine bp sequences (Rebar et al., 1994, Science, 263:671-3; Wolfe et al., 2001, Structure (Camb), 9:717-23; Sera and Uranga, 2002, Biochemistry, 41:7074-81). Thus, one should be able to engineer chimeric nucleases to stimulate gene targeting at any locus. Our data suggest that the most efficient stimulation of gene targeting is obtained when dimers of chimeric nucleases, including heterodimers, cooperate to cleave DNA. Using a pair of three finger chimeric nucleases, the overall recognition sequence would be 18 bp long which statistically should be unique in a 3 billion bp genome. It may not be possible to engineer pairs of chimeric nucleases that cleave at any sequence. Elliot et al. (1998), however, show that gene conversion tract lengths can be up to a hundred base pairs in length even with sequence heterologies (Elliott et al., 1998, Mol Cell Biol, 18:93-101). Given both the window provided by the length of gene conversion tracts and the ability to select and design triplet zinc fingers to recognize a wide array of nine bp binding sites, it seems likely that chimeric nucleases can be designed to stimulate gene targeting at any sequence in the genome. In our study, Applicants found that chimeric nucleases had some toxicity when continuously over-expressed in 293 cells. It may be possible to decrease the toxicity of chimeric nucleases by improving the specificity of the zinc fingers by in vitro selection (Wolfe et al., 2001, Structure (Camb), 9:717-23) or by placing the chimeric nucleases under more regulated control. In summary, this work establishes a basis for the efficient site-specific genomic manipulation in mammalian somatic cells for experimental purposes. Perhaps more importantly, this work establishes a paradigm for correction of mutations by gene targeting in human somatic cells for therapeutic purposes.

Example 2

Site-Specific Manipulation of the Genome with Chimeric Nucleases

Cys2-His2 zinc finger DNA binding domains are modular protein units that can be designed to recognize a wide variety of nucleotide triplets (Wolfe et al., 2000, Annu Rev Biophys Biomol Struct, 29:183-212). For example, using in vitro selection techniques, some research groups have designed zinc fingers that can bind with high specificity to all 16 different GNN nucleotide triplets (Liu et al., 2002, J Biol Chem, 277:3850-3856; Segal et al., 1999, Proc Natl Acad Sci USA, 96:2758-2763). A research group reported a similar characterization of zinc finger domains that could bind all 16 different ANN nucleotide triplets (Dreier et al., 2001, J Biol Chem, 276:29466-29478). Finally, others have proposed a recognition code for all nucleotide triplets (Sera and Uranga, 2002, Biochemistry, 41:7074-7081; Wolfe et al., 2000, Annu Rev Biophys Biomol Struct, 29:183-212). These codes were developed based on the recognition sequences and crystal structures of known zinc finger DNA binding domains. Applicants' prior work established a basis for the rational design of a zinc-finger DNA domain to recognize any triplet.

To design zinc finger domains to recognize endogenous sequences in genes that cause genetic diseases when mutated, Applicants used a PCR based strategy to manufacture three finger zinc finger domains and fused the three finger domain to the endonuclease domain of the FokI restriction enzyme. To assay whether the new chimeric nucleases could stimulate gene targeting, Applicants created an artificial gene target integrated as a single copy in the genome of the cell. The artificial gene target consisted of a GFP gene with an inverted repeat of the 9 bp endogenous target sequence with the 9 bp recognition sequence for Zif268. Applicants have previously shown that the chimeric nuclease with the Zif268 three-finger domain (CMV-Zif-L3-Fn) is able to stimulate gene targeting as a heterodimer. If gene targeting occurs, the mutated GFP gene converts to wild-type and the cell becomes GFP positive. The efficiency of gene targeting is determined by measuring the number of GFP positive cells by flow cytometry.

Applicants provide evidence and proof of principle that chimeric nucleases can be used to stimulate gene targeting at endogenous sequences from important disease causing genes by designing chimeric nucleases to cleave target sequences derived from the human β-globin gene and the human common γ-chain. A point mutation in the human β-globin gene causes sickle cell anemia and a variety of mutations in the common γ-chain lead to severe combined immunodeficiency (SCID).

The sequence of the human R-globin gene surrounding the codon mutated to cause sickle cell anemia is shown in FIG. 4. Depicted are two pairs of potential chimeric nucleases (HBGZF1 and HBGZF2; HBGZF3 and HBGZF4). The binding sites for the chimeric nucleases are highlighted by being in capital letters.

FIG. 5 demonstrates the binding site for HBGZF1 and the zinc finger domains from Liu et al. (2002) and Segall et al. (1999) that recognize each triplet using the single letter code. Applicants made a chimeric nuclease ("HBGZF1") using the amino acids for fingers 1-3 that are denoted by a star and placed the chimeric nuclease under the control of a CMV promoter. Applicants then transfected 293 cells with the artificial GFP gene target (293/1104 cells). The GFP gene contains the insertional mutation as depicted in FIG. 6. Applicants found that transfecting either CMV-HBGZF1 or CMV-Zif-L3-Fn did not significantly stimulate gene targeting (FIG. 6). When Applicants transfected the two nucleases together, however, Applicants obtained significant stimulation of gene targeting (over 4000-fold) and a gene targeting rate almost as high as with the I-SceI endonuclease (FIG. 6). This stimulation of gene targeting demonstrates that chimeric nucleases can be designed to recognize endogenous gene sequences and that those nucleases can then serve to stimulate gene targeting at those sequences.

The design and target site for HBGZF4 is shown in FIG. 7. The top part of FIG. 8 shows the artificial GFP gene target in which the HBGZF4 is placed as an inverted repeat with respect to the ZIF268 binding site. Using cell line 293/1114 that contains a single copy of this gene target, Applicants obtained excellent gene targeting stimulation using the I-SceI endonuclease, but only slight stimulation using CMV-HBGZF4 and CMV-Zif-L3-Fn together (~60 fold). The stimulation with both nucleases was not significantly superior to that obtained using CMV-HBGZF4 alone ~30 fold).

It is known that mutations in the human common γ-chain are the most common cause of SCID (Notarangelo et al., 2000, Immunol Rev, 178:39-48). FIG. 9 shows the structure of the human common γ-chain and the location of mutations in the gene that lead to SCID. The lower part of FIG. 9 shows the sequence of exon 5 and the proposed binding sites for chimeric nucleases HCGCZF1 and HCGCZF2.

FIG. 10 shows the binding site for HCGCZF2 and the structure of HCGCZF2 using the amino acids for zinc fingers 1-3 deduced from the zinc-finger code from Sera and Uranga (2002). The top part of FIG. 11 shows the artificial hybrid HCGCZF2/Zif268 binding site inserted into the GFP gene. Transfecting CMV-HCGCZF2 or CMV-Zif-L3-Fn alone did not significantly stimulate gene targeting. But using the chimeric nucleases together, Applicants obtained significant stimulation in gene targeting (over 200-fold) (FIG. 11). The two nucleases together, however, were not as efficient as the 1-SceI endonuclease (FIG. 11). Nonetheless, HCGCZF2 provides a second example of the empiric design of a chimeric nuclease to recognize an endogenous 9 bp sequence that can stimulate gene targeting in the genome of a human somatic cell.

Example 3

Gene Targeting of Endogenous Sequences

In example 2, applicants demonstrated the design of chimeric nucleases (zinc finger nucleases in this example) to cleave at sequences derived from endogenous genes (the β-globin gene and the common γ-chain gene). In particular applicants were 100% successful at designing chimeric nucleases to cleave at target sites with the following consensus sequence: 5' NNCNNCNNC GNNGNNGNN 3' (SEQ ID NO: 6) where G represents guanine and N represents any nucleotide. Applicants expected, therefore, that one could empirically design a pair of zinc finger nucleases to stimulate gene targeting in a natural gene if that gene contained an inverted repeat of the above consensus sequence with the repeats separated by 6 nucleotides (e.g. 5' NNNNNN GNNGNNGNNC 3', SEQ ID NO: 7). Both the GFP gene and the human CD8α gene contain such a sequence.

In this example, applicants demonstrate the design of chimeric nucleases that stimulate gene targeting in both of these genes.

Gene Targeting of GFP Using GFP Chimeric Nucleases

By searching the sequence of GFP, following sequence was identified: 5' ACC ATC TTC TTCAAG GAC GAC GGC 3' (SEQ ID NO: 10). This sequence fits the inverted repeat consensus sequence described above. The sequence goes from bp 292-315 of the coding sequence of the gene. Using, in part, guidance from Liu et al. (2002) applicants made GFP-CN1 to recognize the target sequence 5' GAA GAT GGT 3' (SEQ ID NO: 11) and GFP-CN2 to recognize the target sequence 5' GAC GAC GGC 3' (SEQ ID NO: 12). Applicants used the chimeric nuclease backbone from Zif-Fn to make each of these and tested the GFP-CNs using the GFP gene targeting system described in example 1 above. The target binding site for the GFP-CNs lies adjacent to the insertion of the I-SceI recognition site into the GFP gene. Briefly, in these cells the mutated GFP gene is integrated as a single copy into the genome of 293 cells. The GFP-CNs were able to stimulate gene targeting when co-transfected with a repair substrate by 1000-fold (FIG. 12). The GFP-CNs were not as efficient as I-SceI at stimulating gene targeting (FIG. 12).

In conclusion this example shows that chimeric nucleases can be generated to stimulate gene targeting at a natural gene even if that gene is integrated into the genome of a human somatic cell.

Gene Targeting of the Human CD8 Gene Using Chimeric Nucleases

In the GFP gene targeting system we express the human CD8α gene off a bicistronic transcript that includes the mutated GFP gene. In cell line 293/1004, for example, 95% of the cells are CD8 positive. Applicants found the following sequence 5' GGCGCCCAC CATCGC GTCGCAGCC 3' (SEQ ID NO: 13) that spans base pair 441-468 of the human CD8α gene and fits the inverted repeat consensus described above. Applicants constructed to recognize 5'

GTGGGCGCC 3' (SEQ ID NO: 14) and to recognize 5' GTCGCAGCC 3' (SEQ ID NO: 15). Applicants also constructed a CD8 cDNA knock-out plasmid in which a puromycin resistance cassette is flanked by 440 bases of 5' homology and 220 bases of 3' homology to the CD8 gene (called "CD8 Knockout Plasmid"). Applicants then transfected the CD8 Knockout Plasmid with and without the CD8 chimeric nucleases into cell line 293/1104 and measured the percentage of CD8 positive cells in a population of cells after puromycin selection (FIG. 13). Transfecting the CD8 Knockout Plasmid did not change the number of CD8 negative cells from the parent population (5% CD8 negative in both) as expected. After co-transfection of the CD8 chimeric nucleases with the CD8 Knockout Plasmid, over 20% of the cells were now CD8 negative. This shows that chimeric nucleases can stimulate gene targeting in the CD8a cDNA by stimulating the insertion of the puromycin knock-out plasmid into the gene.

This example demonstrates that pairs of chimeric nucleases can be designed to stimulate gene targeting in natural genes. In the first case we show that chimeric nucleases can be used to stimulate the repair of the GFP gene as a model for how chimeric nucleases can be designed and used in potential gene therapy applications. In the second case, we show that chimeric nucleases can stimulate gene targeting and the knock-out of the CD8 gene as a model for how chimeric nucleases can be designed and used in potential somatic cell genetic applications. Furthermore, the knock-out of the CD8 gene involved the insertion of a large marker gene into the CD8 locus, demonstrating that the techniques disclosed herein may be used for "transgenesis", i.e., the insertion of a transgene into a desired position of the genome.

EQUIVALENTS

While specific embodiments of the subject inventions are explicitly disclosed herein, the above specification is illustrative and not restrictive. Many variations of the inventions will become apparent to those skilled in the art upon review of this specification and the claims below. The full scope of the inventions should be determined by reference to the claims, along with their full scope of equivalents, and the specification, along with such variations.

The invention claimed is:

1. A method of changing a target sequence in a beta-globin (β-globin) endogenous gene of an isolated mammalian cell, comprising:
   (a) introducing a nucleic acid encoding two chimeric nucleases into the cell, wherein the chimeric nucleases comprise:
      (i) a zinc finger DNA binding domain comprising a zinc finger protein that binds to a target site that comprises SEQ ID NO: 17, SEQ ID NO: 25, SEQ ID NO: 38 or nucleotides 19-27 of SEQ ID NO: 16;
      (ii) a cleavage domain; and
      (iii) a nuclear localization signal;
      whereby the chimeric nucleases are produced in the cell and dimerize to cleave the β-globin endogenous gene; and
   (b) introducing a nucleic acid comprising a repair substrate into the cell, wherein said repair substrate comprises:
      (i) a nucleic acid sequence that is substantially identical to a region surrounding the target sequence; and
      (ii) a nucleic acid sequence which changes the target sequence upon recombination between the repair substrate and the target sequence,
      whereby the endogenous β-globin gene is changed by the repair substrate upon recombination.

2. The method of claim 1, wherein the target sequence contains an allele that contributes to a disease that is repaired by the repair substrate.

3. The method of claim 1, wherein the target sequence is within the sequence of a gene that is attenuated or inactivated by the repair substrate.

4. The method of claim 1, wherein the target sequence is replaced by a heterologous sequence in the repair substrate.

5. The method of claim 4, wherein the heterologous sequence comprises the coding sequence of a transgene.

6. The method of claim 5, wherein the target sequence is selected such that the coding sequence of the transgene is inserted at a transcriptionally active site.

7. The method of claim 1, wherein the nucleic acid encoding the chimeric nuclease and the repair substrate are present in a single vector introduced into the cell.

8. The method of claim 1, wherein the nucleic acid encoding the chimeric nuclease is operably linked to a promoter in a vector.

9. The method of claim 8, wherein the promoter is an inducible promoter.

10. The method of claim 9, wherein the cleavage domain comprises a cleavage domain of a restriction endonuclease.

11. The method of claim 10, wherein the cleavage domain comprises a FokI cleavage domain.

12. The method of claim 1, wherein the chimeric nuclease comprises a heterodimer of two different chimeric nucleases.

13. The method of claim 1, wherein the target sequence includes a mutation that causes sickle-cell anemia.

14. The method of claim 1, wherein the repair substrate is operably linked to a promoter.

15. The method of claim 14, wherein the promoter is an inducible promoter.

16. A method of inactivating an endogenous CD8 gene in an isolated mammalian cell, the method comprising:
   (a) introducing a nucleic acid encoding two chimeric nucleases into the cell, wherein said chimeric nucleases comprise:
      (i) a zinc finger DNA binding domain that binds to a target site in the CD8 gene, wherein the target site comprises nucleotides 19 to 30 of SEQ ID NO: 51 or nucleotides 6 to 14 of SEQ ID NO: 52,
      (ii) a cleavage domain; and
      (iii) a nuclear localization signal;
      whereby the chimeric nucleases are produced in the cell and dimerize to cleave the CD8 endogenous gene; and
   (b) introducing a nucleic acid comprising a repair substrate into the cell, wherein said repair substrate comprises:
      (i) a nucleic acid sequence that is substantially identical to a region surrounding the target sequence; and
      (ii) a nucleic acid sequence which changes the target sequence upon recombination between the repair substrate and the target sequence,
      whereby the endogenous CD8 gene is inactivated by the repair substrate upon recombination.

* * * * *

SEQUENCE LISTING

```
<160> NUMBER OF SEQ ID NOS: 53

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tagggataac agggtaat                                                    18

<210> SEQ ID NO 2
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 ggggaagaa                                                               9

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 gcgtggtcg                                                               9

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
```

```
gatgttgct                                                               9
```

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: a, c, t, g, unknown or other

<400> SEQUENCE: 5

```
gatgnnnnnn ttgct                                                       15
```

<210> SEQ ID NO 6
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (8)..(9)
<223> OTHER INFORMATION: a, c, t, g, unknown or other

<400> SEQUENCE: 6

```
gnngnngnn                                                               9
```

<210> SEQ ID NO 7
<211> LENGTH: 24
<212> TYPE: DNA
<213> ORGANISM: Homo sapiens
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (10)..(15)
<223> OTHER INFORMATION: a, c, t, g, unknown or other
<220> FEATURE:
<221> NAME/KEY: modified_base
<222> LOCATION: (17)..(18)
<223> OTHER INFORMATION: a, c, t, g, unknown or other
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (23)..(24)
<223> OTHER INFORMATION: a, c, t, g, unknown or other

<400> SEQUENCE: 7
nncnncnncn nnnnngnngn ngnn                                          24

<210> SEQ ID NO 8
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 ggggaagaa                                                            9

<210> SEQ ID NO 9
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9 gcgtgggcg                                                            9

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
accatcttct tcaaggacga cggc                                          24

<210> SEQ ID NO 11
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 gaagatggt                                                            9

<210> SEQ ID NO 12
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12 gacgacggc                                                            9

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

```
ggcgcccacc atcgcgtcgc agcc                                            24
```

<210> SEQ ID NO 14
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

```
gtgggcgcc                                                              9
```

<210> SEQ ID NO 15
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
gtcgcagcc                                                              9
```

<210> SEQ ID NO 16
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

```
actagcaacc tcaaacagac accatggtgc atctgactcc tgaggagaag tctgccgtta     60
ctgccctgtg gggcaaggtg aacg                                            84
```

<210> SEQ ID NO 17
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
gaggttgct                                                              9
```

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 18

```
Gln Ser Ser Asp Leu Thr Arg
1               5
```

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

```
<400> SEQUENCE: 19

Thr Ser Gly Glu Leu Val Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 20

Thr Ser Gly Ala Leu Thr Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 21

Thr Ser Gly Ser Leu Thr Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 22

Arg Ser Asp Asn Leu Thr Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 23

Arg Ser Asp Asn Leu Val Arg
1               5

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agcaacctct ctagagcgtg ggcg                                          24

<210> SEQ ID NO 25
<211> LENGTH: 9
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 25 ggcaaggtg                                                                 9

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 26

Arg Ser Asp Ala Leu Thr Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 27

Arg Ser Asn Ser Leu Thr Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 28

Arg Ser Asp Thr Leu Ser Asn
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 29

Arg Lys Asp Asn Leu Lys Asn
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 30

Arg Ser Ser Asn Leu Thr Gln
1               5
```

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 31

Asp Arg Ser His Leu Ala Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 32

Glu Ser Asn His Leu Thr Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 33

Glu Arg Ser Lys Leu Ala Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 34

Asp Pro Gly His Leu Val Arg
1               5

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
caccttgcct ctagagcgtg ggcg                                          24

<210> SEQ ID NO 36
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
gaacaatcag tggattatag acataagttc tccttgccta gtgtggatgg gcagaaacgc    60
tacacgtttc gtgttcggag ccgctttaac ccactctgtg gaagtgctca gcattggagt   120
gaatggagcc acccaatcca ctgggggagc aatacttcaa aagag                    165
```

<210> SEQ ID NO 37
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
gtcttttgaa gtattgctcc cccagtggat tgggtggctc cattcactcc aatgctgagc    60
acttccacag agtgggttaa agcggctccg aacacgaaac gtgtagcgtt tctgcccatc   120
cacactaggc aaggagaact tatgtctata atccactgat tgttc                    165
```

<210> SEQ ID NO 38
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

```
gggggagca                                                              9
```

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 39

Gln Ser Gly Ser Leu Thr Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 40

Gln Ser Gly Asp Leu Thr Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 41

Gln Ser Gly Asp Leu Thr Arg
1               5

```
<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 42

Gln Ser Asn Asp Leu Thr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 43

Gln Ser Gly His Leu Gln Lys
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 44

Gln Arg Ala His Leu Glu Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 45

Gln Ser Ser His Leu Thr Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 46

Arg Ser Asp His Leu Ala Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide
```

```
<400> SEQUENCE: 47

Arg Ser Asp His Leu Thr Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 48

Arg Ser Ser His Leu Thr Arg
1               5

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tgctccccct ctagagcgtg ggcg                                              24

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
accatcttct tcaaggacga cggcaac                                           27

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
accggcgccc accatcgcgt cgcagccctg                                        30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cagggctgcg acgcgatggt gggcgccggt                                        30

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Any amino acid

<400> SEQUENCE: 53

Trp Ser Xaa Trp Ser
1               5
```